(12) United States Patent
Yaoka et al.

(10) Patent No.: US 10,851,533 B2
(45) Date of Patent: Dec. 1, 2020

(54) SANITARY WASHING DEVICE

(71) Applicant: TOTO LTD., Kitakyushu (JP)

(72) Inventors: Toshinari Yaoka, Kitakyushu (JP);
Minoru Sato, Kitakyushu (JP);
Keisuke Tashiro, Kitakyushu (JP);
Satoru Matsumoto, Kitakyushu (JP);
Shogo Kanda, Kitakyushu (JP); Yo Morotomi, Kitakyushu (JP)

(73) Assignee: TOTO LTD., Fukuoka (JP)

( * ) Notice: Subject to any disclaimer, the term of this patent is extended or adjusted under 35 U.S.C. 154(b) by 0 days.

(21) Appl. No.: 16/413,710

(22) Filed: May 16, 2019

(65) Prior Publication Data
US 2019/0368181 A1 Dec. 5, 2019

(30) Foreign Application Priority Data

Jun. 1, 2018 (JP) .................................. 2018-106338
Apr. 9, 2019 (JP) .................................. 2019-074091

(51) Int. Cl.
*E03D 9/08* (2006.01)
*A61L 2/08* (2006.01)
*A61L 2/18* (2006.01)

(52) U.S. Cl.
CPC .............. *E03D 9/08* (2013.01); *A61L 2/084* (2013.01); *A61L 2/186* (2013.01); *A61L 2202/11* (2013.01)

(58) Field of Classification Search
CPC ........... E03D 9/08; E03D 9/002; E03D 11/11; A47K 13/30; A47K 13/302; A47K 17/00;
(Continued)

(56) References Cited

U.S. PATENT DOCUMENTS 4,670,917 A * 6/1987 Kuo .......................... E03D 9/08
4/420.4
4,704,748 A * 11/1987 Takeda ...................... E03D 9/08
4/420.4
(Continued)

FOREIGN PATENT DOCUMENTS

CN 104368020 A 2/2015
JP 2002285615 A * 10/2002
(Continued)

OTHER PUBLICATIONS

English translation of Taiwanese Office Action for Application No. 108114868, dated Sep. 23, 2019.
(Continued)

*Primary Examiner* — Patrick M. Buechner
(74) *Attorney, Agent, or Firm* — Pearne & Gordon LLP

(57) ABSTRACT

The toilet device includes a toilet 800 and a sanitary washing device 100 mounted on the toilet 800. The sanitary washing device 100 includes a nozzle 473, a casing 400, a toilet seat 200, a toilet lid 300, and an illuminator 700. When the user operates an operation part 500 built into the interior of the casing 400, the nozzle 473 is advanced into the bowl 801 of the toilet 800. The casing 400 includes a nozzle container 480 that can store the entire nozzle 473. The illuminator 700 irradiates sterilizing light which is light having a sterilizing action. The illuminator 700 irradiates the sterilizing light L directly on the front surface 473a of the nozzle 473 and/or the part 480c of the bottom surface part 480b positioned below the front surface 473a.

12 Claims, 19 Drawing Sheets

(58) Field of Classification Search
CPC . A47K 3/001; A47K 7/04; A47K 7/08; A61H 2033/0008; A61H 2033/0083; A61H 2201/0188; A61L 2/08; A61L 2/081; A61L 2/082; A61L 2/084; A61L 2/085; A61L 2/087; A61L 2/088; A61L 2/10; A61L 2/12; A61L 2/16; A61L 2/18; A61L 2/183; A61L 2/186; A61L 2202/11; A61L 2202/20

See application file for complete search history.

(56) References Cited

U.S. PATENT DOCUMENTS

| | | | | |
|---|---|---|---|---|
| 4,841,582 A * | 6/1989 | Matsui | | E03D 9/08 4/420.1 |
| 5,025,511 A * | 6/1991 | Takeda | | E03D 9/08 4/444 |
| 5,292,479 A * | 3/1994 | Haraga | | A24F 19/00 4/216 |
| 6,754,912 B1 * | 6/2004 | Hayashi | | E03D 9/08 239/468 |
| 2001/0022006 A1 * | 9/2001 | Tomita | | B05B 1/3478 4/420.4 |
| 2006/0085902 A1 * | 4/2006 | Lee | | E03D 9/08 4/420.4 |
| 2007/0256226 A1 * | 11/2007 | Pinizzotto | | E03D 9/08 4/420.4 |
| 2010/0162475 A1 * | 7/2010 | Hashidume | | E03D 9/08 4/233 |
| 2010/0269247 A1 * | 10/2010 | Chen | | E03D 9/08 4/229 |
| 2011/0030133 A1 * | 2/2011 | Morotomi | | E03D 9/08 4/443 |
| 2012/0261590 A1 * | 10/2012 | Boyle | | A61L 2/24 250/453.11 |
| 2013/0133131 A1 * | 5/2013 | Peng | | A47K 13/24 4/444 |
| 2013/0185861 A1 * | 7/2013 | Matsumoto | | E03D 9/005 4/443 |
| 2015/0048260 A1 | 2/2015 | Chui et al. | | |
| 2018/0238037 A1 | 8/2018 | Komatsu et al. | | |
| 2019/0071856 A1 * | 3/2019 | Park | | B05B 13/0415 |

FOREIGN PATENT DOCUMENTS

| | | | |
|---|---|---|---|
| JP | 2006-274641 A | | 10/2006 |
| JP | 2006274641 A | * | 10/2006 |
| JP | 2010-084335 A | | 4/2010 |
| JP | 2010-084356 A | | 4/2010 |
| JP | 2013083141 A | * | 5/2013 |
| TW | I365245 B | | 6/2012 |

OTHER PUBLICATIONS

English translation of Japanese Publication No. 2013-083141A dated May 9, 2013 in the name of Kwareukyutar Co. Ltd.

* cited by examiner

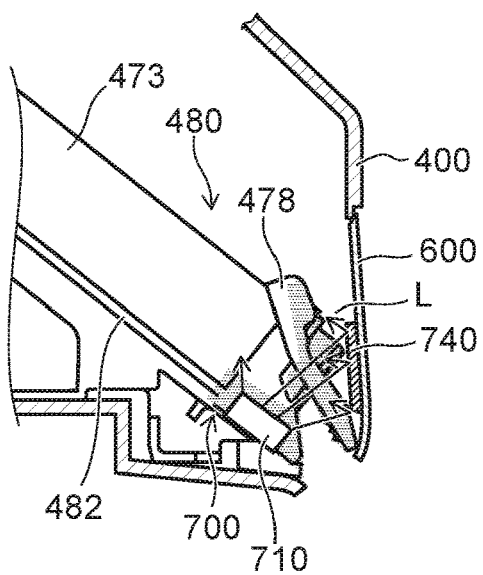
FIG. 9A
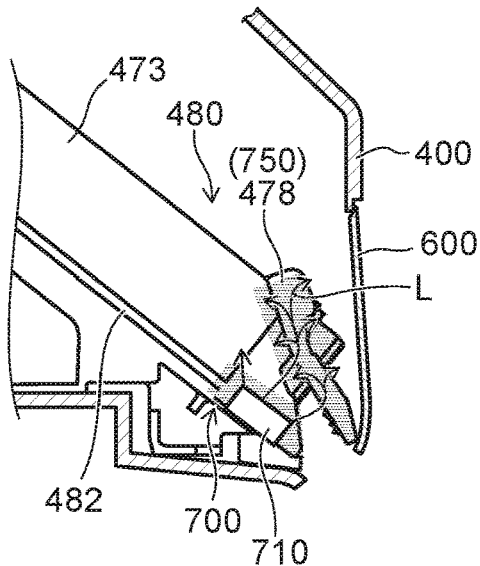
FIG. 9B
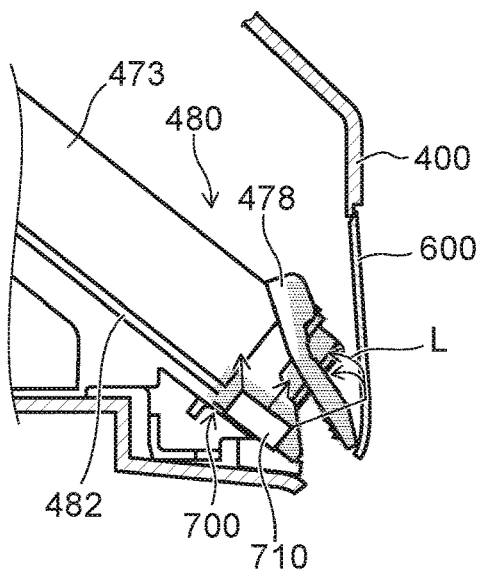
FIG. 9C
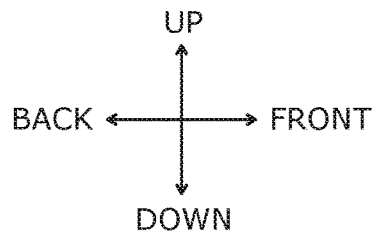

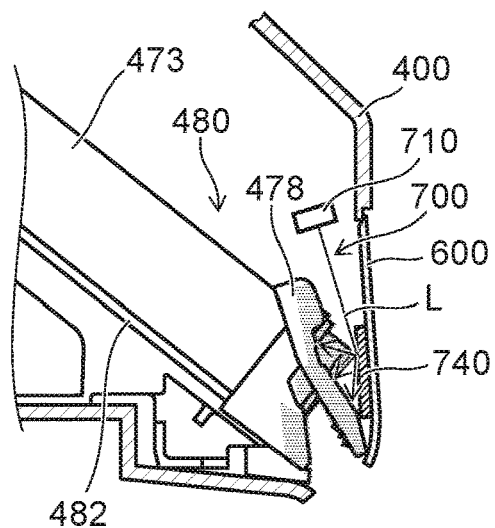
FIG. 10A
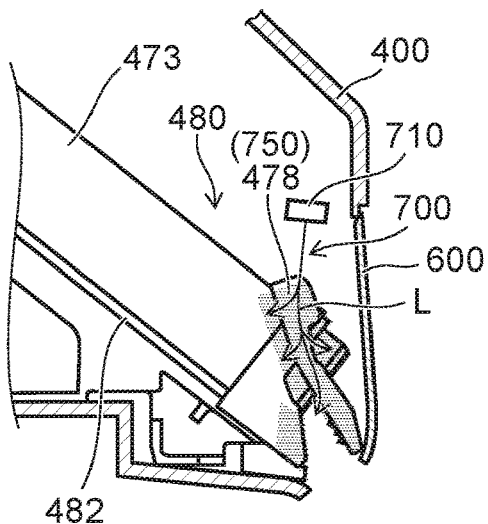
FIG. 10B
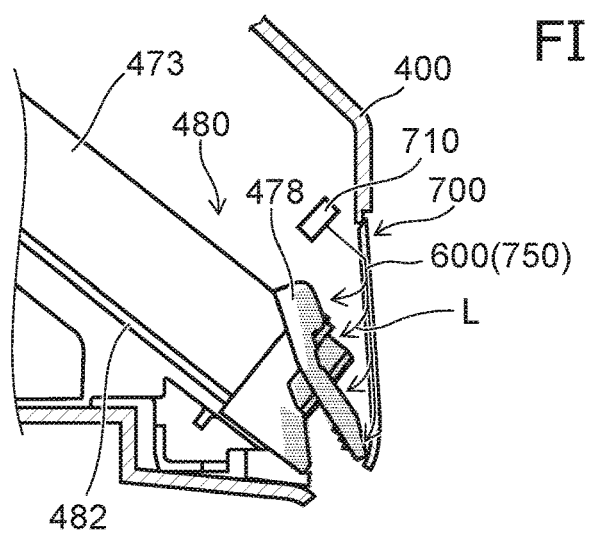
FIG. 10C
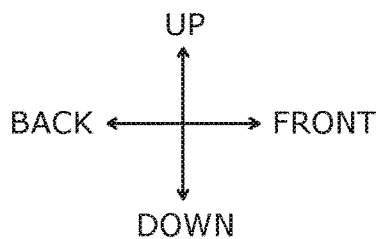

SANITARY WASHING DEVICE

CROSS-REFERENCE TO RELATED APPLICATIONS

This application is based upon and claims the benefit of priority from Japanese Patent Application No. 2018-106338, filed on Jun. 1, 2018; and Japanese Patent Application No. 2019-074091, filed on Apr. 9, 2019; the entire contents of which are incorporated herein by reference.

FIELD

Embodiments described herein relate generally to a sanitary washing device.

BACKGROUND

A sanitary washing device that includes a private part wash nozzle is discussed in JP-A 2013-83141 (Kokai). To remove dirt adhered to the private part wash nozzle in the sanitary washing device, washing water is squirted onto the private part wash nozzle; and UV light that has a sterilizing action is irradiated toward the private part wash nozzle.

According to the technology discussed in JP-A 2013-83141 (Kokai), it is possible to suppress the dirt of the private part wash nozzle. In JP-A 2013-83141 (Kokai), an aspect is discussed in which the UV light is irradiated from above the private part wash nozzle, and is irradiated not only on the private part wash nozzle but also on peripheral parts. However, because the private part wash nozzle has a tilted disposition, the upper part of the private part wash nozzle is in a shadow even when the UV light is irradiated from above the private part wash nozzle. The UV light is not irradiated on the front surface of the private part wash nozzle and the nozzle container positioned below the private part wash nozzle. Therefore, the dirt of the nozzle container cannot be suppressed sufficiently by the technology of JP-A 2013-83141 (Kokai).

Dirt due to the adhesion of feces and/or urine exists at the nozzle container. Also, visible dirt exists at the nozzle container due to bacteria and mold that floats around inside the toilet space and adheres to and proliferates in the water adhered to the nozzle container due to the private part wash, the self-cleaning of the nozzle, etc. The nozzle container is visible when the user opens the nozzle lid to clean the sanitary washing device, etc., or when the nozzle lid opens for the nozzle to advance in the nozzle cleaning. If the user perceives the adhesion of bacteria or mold on the nozzle container, the user may feel uneasy about the cleanliness of the private part wash nozzle even when the private part wash nozzle itself is clean. As a result, there is a risk that a highly cleanliness-conscious user may no longer use the private part wash nozzle.

SUMMARY

According to the embodiment, a sanitary washing device, comprises a private part wash nozzle, a drive device, a casing, and an illuminator; the private part wash nozzle is tilted downward toward a front side and has a water discharge hole discharging washing water toward a private part of a user; the drive device causes the private part wash nozzle to advance and retract; the casing includes a nozzle container that can store an entirety of the private part wash nozzle in a state in which the private part wash nozzle is retracted; the illuminator irradiates sterilizing light which is light having a sterilizing action; and the illuminator irradiates the sterilizing light on at least a front surface of the private part wash nozzle and a part of a bottom surface part of the nozzle container positioned below the front surface.

BRIEF DESCRIPTION OF THE DRAWINGS

FIG. 9A to FIG. 9C are cross-sectional views illustrating examples of the private part wash nozzle periphery of the sanitary washing device according to the embodiment;

FIG. 10A to FIG. 10C are cross-sectional views illustrating other examples of the private part wash nozzle periphery of the sanitary washing device according to the embodiment;

DETAILED DESCRIPTION

Figure 1:
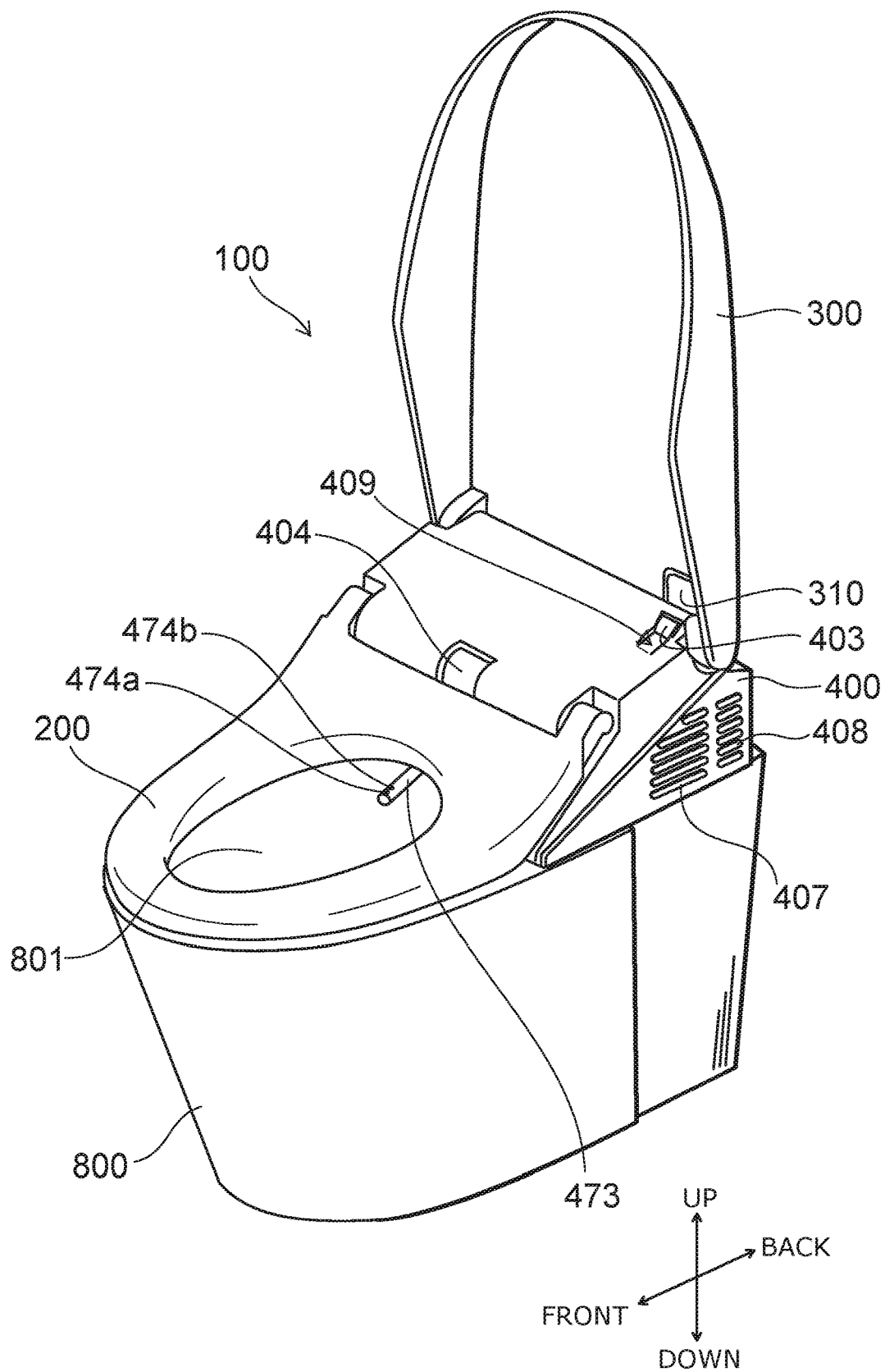
FIG. 1 is a perspective view illustrating a toilet device including a sanitary washing device according to an embodiment.

A first invention is a sanitary washing device, comprising a private part wash nozzle, a drive device, a casing, and an illuminator; the private part wash nozzle is tilted downward toward a front side and has a water discharge hole discharging washing water toward a private part of a user; the drive device causes the private part wash nozzle to advance and retract; the casing includes a nozzle container that can store an entirety of the private part wash nozzle in a state in which the private part wash nozzle is retracted; the illuminator irradiates sterilizing light which is light having a sterilizing action; and the illuminator irradiates the sterilizing light on at least a front surface of the private part wash nozzle and a part of a bottom surface part of the nozzle container positioned below the front surface.

According to the sanitary washing device, the illuminator irradiates the sterilizing light on the front surface of the private part wash nozzle and the part of the bottom surface part of the nozzle container positioned below the front surface. These regions are a visible region that is visible to the user. By the irradiation of the sterilizing light, the adhesion of dirt in the visible region of the private part wash nozzle and inside the nozzle container can be suppressed. Thereby, the user can be caused to perceive that the private part wash nozzle is clean and the nozzle container where the private part wash nozzle is stored is clean. Therefore, even a highly cleanliness-conscious user can use the private part wash nozzle with peace of mind.

A second invention is the sanitary washing device of the first invention, wherein the illuminator is configured to cause an average illuminance of the sterilizing light on the front surface and a part of the nozzle container positioned frontward of the front surface to be larger than an average illuminance of the sterilizing light on an outer perimeter surface of the private part wash nozzle.

According to the sanitary washing device, the sterilizing light is irradiated with particular emphasis on the visible region of the private part wash nozzle and the nozzle container. Therefore, dirt adheres less easily to the visible region where high cleanliness is necessary. In recent years, it has become desirable to downsize sanitary washing devices to improve the designability. By setting the average illuminance on the outer perimeter surface of the private part wash nozzle to be smaller than in the visible region of the nozzle container, unnecessary irradiation of the sterilizing light can be suppressed; and the electrical power that is applied to the illuminator can be small. The heat generation of the illuminator decreases as the electrical power decreases. Thereby, the heat sink or the like that dissipates the heat of the illuminator can be small; and the illuminator can be downsized. As a result, the sanitary washing device can be downsized.

A third invention is the sanitary washing device of the first or second invention, wherein the illuminator is configured to cause an irradiation area of the sterilizing light on the front surface and a part of the nozzle container positioned frontward of the front surface to be wider than an irradiation area of the sterilizing light on an outer perimeter surface of the private part wash nozzle.

According to the sanitary washing device, the sterilizing light is irradiated with particular emphasis on the visible region of the nozzle container. Therefore, dirt adheres less easily to the visible region where high cleanliness is necessary. In recent years, it has become desirable to downsize sanitary washing devices to improve the designability. By setting the average illuminance on the outer perimeter surface of the private part wash nozzle to be smaller than the visible region of the nozzle container, the unnecessary irradiation of the sterilizing light can be suppressed; and the electrical power that is applied to the illuminator can be small. The heat generation of the illuminator decreases as the electrical power decreases. Thereby, the heat sink or the like that dissipates the heat of the illuminator can be small; and the illuminator can be downsized. As a result, the sanitary washing device can be downsized.

A fourth invention is the sanitary washing device of any one of the first to third inventions, further comprising a nozzle lid provided to be openable and closable with respect to an opening provided at a front end of the nozzle container; the nozzle lid causes the nozzle container to be open in a state in which the private part wash nozzle is advanced and causes the nozzle container to be closed in a state in which the entirety of the private part wash nozzle is stored inside the nozzle container; the nozzle lid has a back surface positioned on the nozzle container side; at least a part of the back surface is formed of a reflective material; and the illuminator directly irradiates at least a part of the sterilizing light on the back surface of the nozzle lid in a state in which the nozzle lid is closed.

According to the sanitary washing device, the adhesion of dirt on the back surface of the nozzle lid can be suppressed because the sterilizing light is directly irradiated on the back surface of the nozzle lid. The back surface of the nozzle lid faces a wide area of the visible region of the private part wash nozzle and the nozzle container. Because the back surface is formed of the reflective material, the sterilizing light that is reflected by the back surface is irradiated in a wide area of the visible region. Thereby, the sterilizing light can be irradiated in a wide area of the visible region even when the illuminator is downsized.

A fifth invention is the sanitary washing device of the fourth invention, wherein the illuminator is configured to cause an irradiation area of the sterilizing light directly irradiated on the back surface of the nozzle lid to be wider than an irradiation area of the sterilizing light directly irradiated on a part of the nozzle lid other than the back surface.

According to the sanitary washing device, the irradiation area of the sterilizing light directly irradiated on the back surface of the nozzle lid can be large. Thereby, the sterilizing light that is reflected by the back surface of the nozzle lid can be irradiated on a wider area of the visible region.

A sixth invention is the sanitary washing device of the fourth or fifth invention, wherein the sterilizing light includes reflected light reflected by the nozzle lid, and direct light not reflected by the nozzle lid; and the illuminator is disposed at a position to cause the direct light to be irradiated on a front end part of the bottom surface part of the nozzle container.

The inventors discovered that the water remaining inside the nozzle container remains easily at the front end part of the bottom surface part of the nozzle container, and that the front end part is dirtied most easily. According to the sanitary washing device, direct light that has a strong sterilizing power can be irradiated on the front end part which is the visible region where dirt occurs most easily. As a result, the occurrence of bacteria and mold on the front end part can be suppressed.

A seventh invention is the sanitary washing device of the sixth invention, wherein the illuminator is disposed to cause the direct light and the reflected light to be irradiated on a front end part of the bottom surface part.

According to the sanitary washing device, both the direct light and the reflected light are irradiated on the front end part of the bottom surface part where the dirt occurs most easily. Therefore, the occurrence of bacteria and mold can be suppressed also at the part of the visible region where the water remains easily.

An eighth invention is the sanitary washing device of any one of the fourth to seventh inventions, wherein the back surface of the nozzle lid is formed in a curved configuration to cause reflected light to diffuse.

According to the sanitary washing device, the sterilizing light that is reflected by the back surface can be diffused more than when the back surface of the nozzle lid has a planar configuration. Thereby, the sterilizing light can be irradiated on a wider area of the visible region.

A ninth invention is the sanitary washing device of any one of the fourth to eighth inventions, wherein the nozzle washer is provided at a front end part vicinity of the private part wash nozzle; the nozzle washer has a nozzle wash hole discharging washing water onto an outer surface of the private part wash nozzle; and the nozzle washer is formed of a transmissive material transmitting the sterilizing light.

According to the sanitary washing device, sterilizing light L that passes through the nozzle washer is irradiated in the visible region positioned in the shadow of the illuminator and in a gap between the private part wash nozzle and the nozzle washer. Thereby, the sterilizing light can be irradiated on a wider area of the visible region.

A tenth invention is the sanitary washing device of the ninth invention, wherein the nozzle washer is configured to cause the sterilizing light to diffuse when being transmitted; and at least a part of the nozzle washer is disposed frontward of the front surface of the private part wash nozzle in a state in which the entirety of the private part wash nozzle is stored inside the nozzle container.

According to the sanitary washing device, by disposing the nozzle washer having the light diffusion effect frontward of the front surface of the private part wash nozzle, the sterilizing light can reach a wider area of the visible region due to the light diffusion effect of the nozzle washer.

An eleventh invention is the sanitary washing device of the tenth invention, wherein the nozzle washer is moved in a state in which the illuminator is operated.

According to the sanitary washing device, the diffusion direction of the light due to the nozzle washer can be changed by moving the nozzle washer in the state in which the illuminator is operated. Thereby, the sterilizing light can be irradiated on a wider area of the visible region.

A twelfth invention is the sanitary washing device of the eleventh invention, wherein the nozzle washer is moved without opening the nozzle lid in the state in which the illuminator is operated.

According to the sanitary washing device, the nozzle washer is moved so that the nozzle lid is not opened. Because the nozzle lid is not open when operating the illuminator, leaking of the sterilizing light outside the casing can be suppressed. Thereby, the sterilizing light can be irradiated on a wider area of the visible region while increasing the safety of the user.

Embodiments of the invention will now be described with reference to the drawings. Similar components in the drawings are marked with the same reference numerals; and a detailed description is omitted as appropriate.

FIG. 1 is a perspective view illustrating a toilet device including a sanitary washing device according to an embodiment.

As illustrated in FIG. 1, the toilet device includes a sit-down flush toilet (for convenience of description hereinbelow, called simply the "toilet") 800 and a sanitary washing device 100 mounted on the sit-down flush toilet 800. The sanitary washing device 100 includes a casing 400, a toilet seat 200, and a toilet lid 300. The toilet seat 200 and the toilet lid 300 each are pivotally supported openably and closeably with respect to the casing 400.

A body wash functional part that realizes the washing of a "bottom" or the like of a user sitting on the toilet seat 200, etc., are built into the interior of the casing 400. For example, a seat contact detection sensor 404 that detects the user being seated on the toilet seat 200 is provided in the casing 400. When the seat contact detection sensor 404 detects the user sitting on the toilet seat 200, a private part wash nozzle (for convenience of description hereinbelow, called simply the "nozzle") 473 can be caused to advance into a bowl 801 of the toilet 800 or retract from the interior of the bowl 801 when the user operates an operation part 500 such as, for example, a remote control, etc. (referring to FIG. 2). A state in which the nozzle 473 is advanced into the bowl 801 is illustrated in the sanitary washing device 100 illustrated in FIG. 1.

The nozzle 473 washes the human private part by discharging water (washing water) toward the human private part. A bidet wash water discharge port 474a and a bottom wash water discharge port 474b are provided in the tip part of the nozzle 473. The nozzle 473 can wash a private part of a female sitting on the toilet seat 200 by squirting water from the bidet wash water discharge port 474a provided in the tip of the nozzle 473. Or, the nozzle 473 can wash the "bottom" of the user sitting on the toilet seat 200 by squirting water from the bottom wash water discharge port 474b provided in the tip of the nozzle 473. In this specification, "water" includes not only cold water but also hot water that is heated.

The modes of washing the "bottom" include, for example, a "bottom wash" and a "gentle wash" that gently washes using a water stream that is softer than that of the "bottom wash." For example, the nozzle 473 can perform the "bidet wash," the "bottom wash," and the "gentle wash."

In the nozzle 473 illustrated in FIG. 1, the bidet wash water discharge port 474a is provided further toward the tip side of the nozzle 473 than is the bottom wash water discharge port 474b. The mounting positions of the bidet wash water discharge port 474a and the bottom wash water discharge port 474b are not limited to the example. The bidet wash water discharge port 474a may be provided further toward the back end side of the nozzle 473 than is the bottom wash water discharge port 474b. Although two water discharge ports are provided in the nozzle 473 illustrated in FIG. 1, three or more water discharge ports may be provided.

Figure 2:
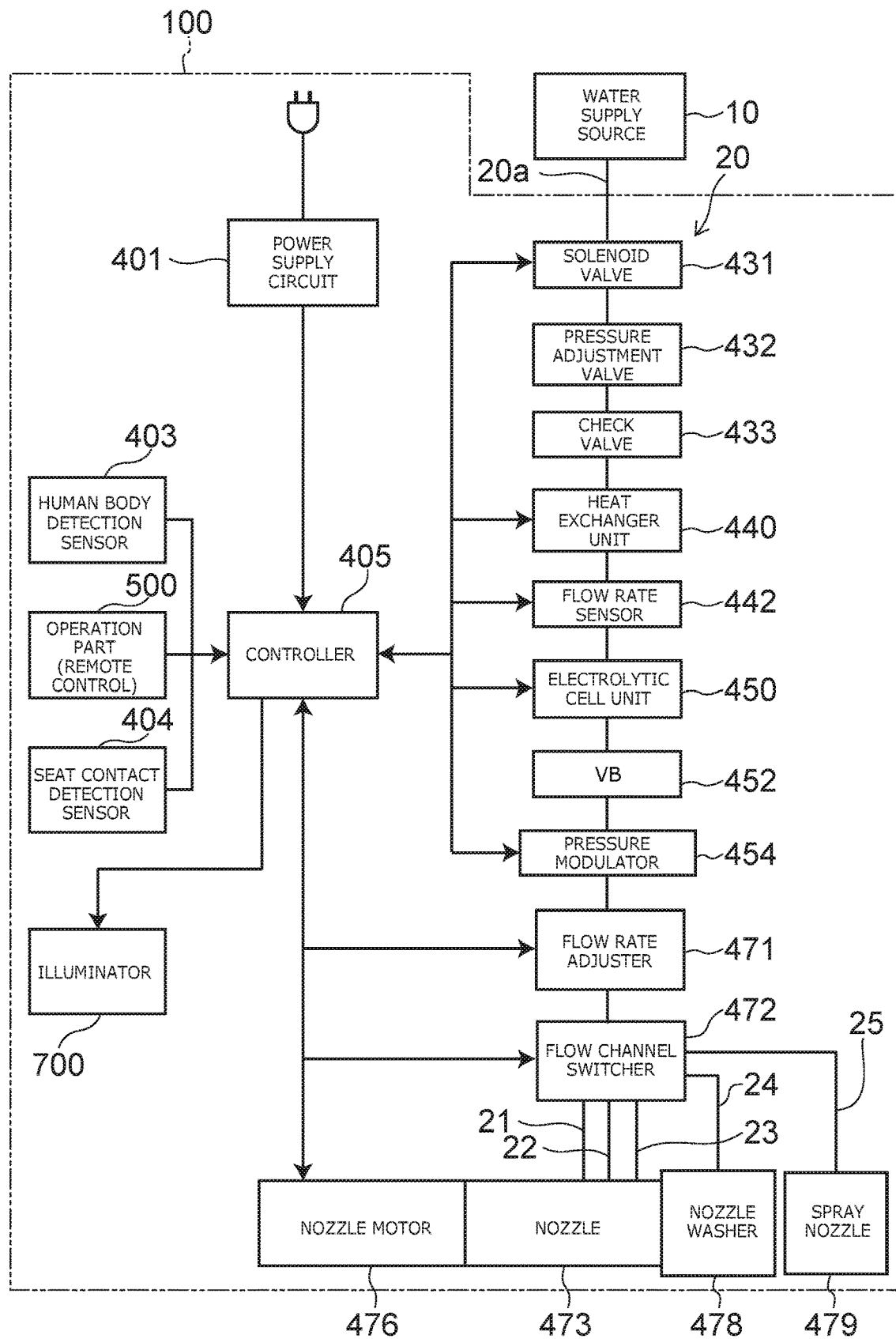
FIG. 2 is a block diagram illustrating the relevant components of the sanitary washing device according to the embodiment.

FIG. 2 is a block diagram illustrating the relevant components of the sanitary washing device according to the embodiment.

The relevant components of the water channel system and the electrical system are illustrated together in FIG. 2.

As illustrated in FIG. 2, the sanitary washing device 100 includes a conduit 20. The conduit 20 includes a pipe line 20a that reaches the nozzle 473 from a water supply source 10 such as a service water line, a water storage tank, etc. The conduit 20 guides the water supplied from the water supply source 10 to the nozzle 473 via the pipe line 20a. For example, the pipe line 20a is formed of components such as a solenoid valve 431, a heat exchanger unit 440, a flow channel switcher 472, etc., described below and multiple pipes that connect these components.

The solenoid valve 431 is provided at the upstream side of the conduit 20. The solenoid valve 431 is an openable and closable solenoid valve and controls the supply of the water based on a command from a controller 405 provided in the interior of the casing 400. In other words, the solenoid valve 431 opens and closes the pipe line 20a. The water that is supplied from the water supply source 10 flows in the pipe line 20*a* by setting the solenoid valve 431 to the open state.

A pressure adjustment valve 432 is provided downstream of the solenoid valve 431. The pressure adjustment valve 432 adjusts the pressure inside the pipe line 20*a* to be within a prescribed pressure range when the water supply pressure is high. A check valve 433 is provided downstream of the pressure adjustment valve 432. The check valve 433 suppresses the backward flow of water upstream of the check valve 433 when the pressure inside the pipe line 20*a* decreases, etc.

The heat exchanger unit 440 (the heater) is provided downstream of the check valve 433. The heat exchanger unit 440 includes a heater and heats the water supplied from the water supply source 10 to, for example, a specified temperature. In other words, the heat exchanger unit 440 produces warm water.

The heat exchanger unit 440 is, for example, an instantaneous-heating (instantaneous type) heat exchanger that uses a ceramic heater, etc. Compared to a stored-hot-water heat exchanger that uses a hot water storage tank, the instantaneous-heating heat exchanger can heat the water to the specified temperature in a short period of time. The heat exchanger unit 440 is not limited to the instantaneous-heating heat exchanger and may be a stored-hot-water heat exchanger. The heater is not limited to examples in which a heat exchanger is used. For example, another heating technique such as microwave heating, etc., may be used as the heater.

The heat exchanger unit 440 is connected to the controller 405. For example, the controller 405 heats the water to the temperature set by the operation part 500 by controlling the heat exchanger unit 440 according to an operation of the operation part 500 by the user.

A flow rate sensor 442 is provided downstream of the heat exchanger unit 440. The flow rate sensor 442 detects the flow rate of the water discharged from the heat exchanger unit 440. In other words, the flow rate sensor 442 detects the flow rate of the water flowing through the pipe line 20*a*. The flow rate sensor 442 is connected to the controller 405. The flow rate sensor 442 inputs the detection result of the flow rate to the controller 405.

An electrolytic cell unit 450 is provided downstream of the flow rate sensor 442. The electrolytic cell unit 450 produces a liquid (functional water) including hypochlorous acid from the service water by electrolyzing the service water flowing through the interior of the electrolytic cell unit 450. The electrolytic cell unit 450 is connected to the controller 405. The electrolytic cell unit 450 produces the functional water based on a control by the controller 405.

The functional water that is produced by the electrolytic cell unit 450 may be, for example, a solution including metal ions such as silver ions, copper ions, etc. Or, the functional water that is produced by the electrolytic cell unit 450 may be a solution including electrolytic chlorine, ozone, etc. Or, the functional water that is produced by the electrolytic cell unit 450 may be acidic water or alkaline water.

A vacuum breaker (VB) 452 is provided downstream of the electrolytic cell unit 450. The vacuum breaker 452 includes, for example, a flow channel where the water flows, an intake port for intaking air into the flow channel, and a valve mechanism that opens and closes the intake port. For example, when water is flowing in the flow channel, the valve mechanism seals the intake port; and when the flow of the water stops, the valve mechanism intakes air into the flow channel by opening the intake port. In other words, the vacuum breaker 452 intakes air into the pipe line 20*a* when the water does not flow in the conduit 20. The valve mechanism includes, for example, a float valve.

As recited above, the vacuum breaker 452 intakes air into the pipe line 20*a*. For example, water drainage of the part of the pipe line 20*a* downstream of the vacuum breaker 452 is promoted thereby. For example, the vacuum breaker 452 promotes the water drainage of the nozzle 473. Thus, because the vacuum breaker 452 drains the water inside the nozzle 473 and intakes air into the nozzle 473, for example, the undesirable backward flow toward the water supply source 10 (the tap water) side of the washing water inside the nozzle 473, the liquid waste collected inside the bowl 801, etc., is suppressed.

A pressure modulator 454 is provided downstream of the vacuum breaker 452. The pressure modulator 454 applies a pulsatory motion or an acceleration to the flow of the water inside the pipe line 20*a* of the conduit 20. Thereby, a pulsatory motion is applied to the water discharged from the bidet wash water discharge port 474*a* and the bottom wash water discharge port 474*b* of the nozzle 473 and the water discharged from the water discharger of a nozzle washer 478. In other words, the pressure modulator 454 causes the fluidic state of the water flowing through the pipe line 20*a* to fluctuate. The pressure modulator 454 is connected to the controller 405. The pressure modulator 454 causes the fluidic state of the water to fluctuate based on a control by the controller 405. The pressure modulator 454 causes the pressure of the water inside the pipe line 20*a* to fluctuate.

A flow rate adjuster 471 is provided downstream of the pressure modulator 454. The flow rate adjuster 471 adjusts the water force (the flow rate). The flow channel switcher 472 is provided downstream of the flow rate adjuster 471. The flow channel switcher 472 performs opening and closing and switching of the water supply to the nozzle 473 and/or the nozzle washer 478. The flow rate adjuster 471 and the flow channel switcher 472 may be provided as one unit. The flow rate adjuster 471 and the flow channel switcher 472 are connected to the controller 405. The operations of the flow rate adjuster 471 and the flow channel switcher 472 are controlled by the controller 405.

The nozzle 473, the nozzle washer 478, and a spray nozzle 479 are provided downstream of the flow channel switcher 472. The nozzle 473 receives a drive force from a nozzle motor 476, advances into the bowl 801 of the toilet 800, and retracts from the interior of the bowl 801. That is, the nozzle motor 476 is a drive device that causes the nozzle 473 to advance and retract based on a command from the controller 405.

For example, the nozzle washer 478 washes the outer surface (the central body) of the nozzle 473 by squirting water or functional water from a water discharger. The outer surface of the nozzle 473 includes, for example, the front surface of the nozzle 473 and the outer perimeter surface of the nozzle 473. The spray nozzle 479 sprays the washing water or the functional water into the bowl 801 in a mist form. In the example, the spray nozzle 479 is provided separately from the nozzle 473 for washing the human body. This is not limited thereto; and a water discharge port for spraying a mist-like liquid into the bowl 801 may be provided in the nozzle 473.

A bottom wash flow channel 21, a gentle wash flow channel 22, and a bidet wash flow channel 23 are provided downstream of the flow channel switcher 472. The bottom wash flow channel 21 and the gentle wash flow channel 22 guide, toward the bottom wash water discharge port 474*b*, the water supplied from the water supply source 10 or the functional water produced by the electrolytic cell unit 450 via the conduit 20. The bidet wash flow channel 23 guides, toward the bidet wash water discharge port 474a, the water supplied from the water supply source 10 or the functional water produced by the electrolytic cell unit 450 via the conduit 20.

A surface wash flow channel 24 and a spray flow channel 25 are provided downstream of the flow channel switcher 472. The surface wash flow channel 24 guides, toward the water discharger of the nozzle washer 478, the water supplied from the water supply source 10 or the functional water produced by the electrolytic cell unit 450 via the conduit 20. The spray flow channel 25 guides, toward the spray nozzle 479, the water supplied from the water supply source 10 or the functional water produced by the electrolytic cell unit 450 via the conduit 20.

By controlling the flow channel switcher 472, the controller 405 switches the opening and closing of the flow channels of the bottom wash flow channel 21, the gentle wash flow channel 22, the bidet wash flow channel 23, the surface wash flow channel 24, and the spray flow channel 25. Thus, the flow channel switcher 472 switches between the state of communicating with the pipe line 20a and the state of not communicating with the pipe line 20a for each of the multiple water discharge ports of the bidet wash water discharge port 474a, the bottom wash water discharge port 474b, the nozzle washer 478, the spray nozzle 479, etc.

Electrical power is supplied to the controller 405 from a power supply circuit 401. The controller 405 controls the operations of the solenoid valve 431, the heat exchanger unit 440, the electrolytic cell unit 450, the pressure modulator 454, the flow rate adjuster 471, the flow channel switcher 472, the nozzle motor 476, etc., based on signals transmitted from a human body detection sensor 403, the seat contact detection sensor 404, the flow rate sensor 442, the operation part 500, etc.

For example, the controller 405 controls an illuminator 700 based on detection information of the human body detection sensor 403 and/or the seat contact detection sensor 404. The illuminator 700 irradiates, onto the periphery of the nozzle 473 (the nozzle container described below), sterilizing light which is light having a sterilizing action. The illuminator 700 is described below.

As illustrated in FIG. 1, the human body detection sensor 403 is provided to be sunk into a recessed part 409 formed in the upper surface of the casing 400. The human body detection sensor 403 detects the user (the human body) approaching the toilet seat 200. In other words, the human body detection sensor 403 detects the user at the vicinity of the sanitary washing device 100. A transmissive window 310 is provided at the back part of the toilet lid 300. Therefore, the human body detection sensor 403 can detect the existence of the user via the transmissive window 310 in the state in which the toilet lid 300 is closed. For example, the controller 405 responds to the detection of the user by the human body detection sensor 403 by automatically opening the toilet lid 300.

Various mechanisms such as a "warm air drying function," a "deodorizing unit," a "room heating unit," etc., may be provided as appropriate in the casing 400. The "warm air drying function" dries the "bottom" or the like of the user sitting on the toilet seat 200 by blowing warm air toward the "bottom" or the like. When these mechanisms are provided, an exhaust port 407 from the deodorizing unit and an outlet 408 from the room heating unit are provided as appropriate in the side surface of the casing 400. However, in the invention, the sanitary washing functional parts or the other additional functional parts may not always be provided.

FIG. 3A, FIG. 3B, FIG. 6, FIG. 7A, and FIG. 7B are cross-sectional views illustrating the private part wash nozzle periphery of the sanitary washing device according to the embodiment.

Figure 4:
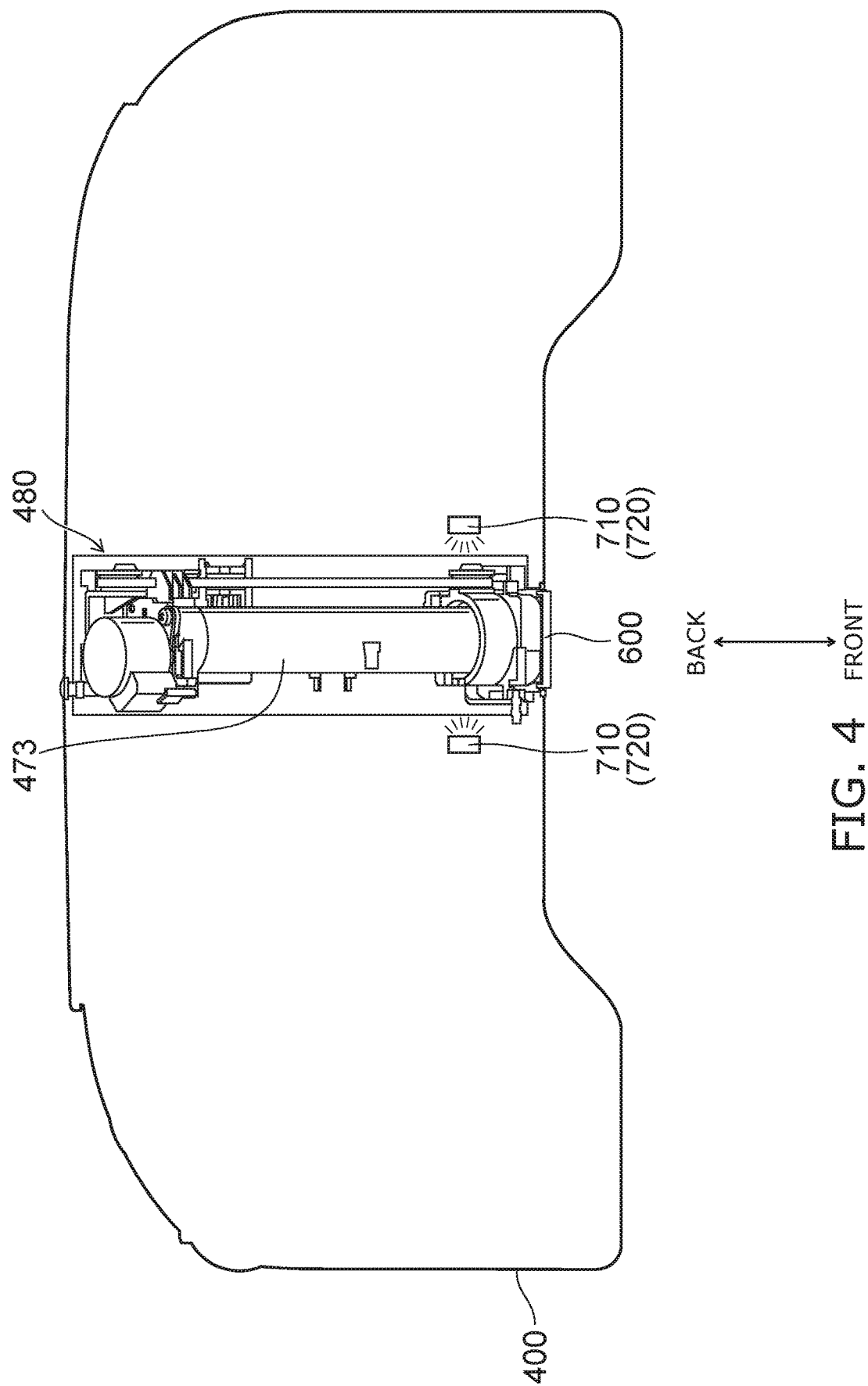
FIG. 4 is a plan view illustrating the internal structure of the sanitary washing device according to the embodiment.

FIG. 4 is a plan view illustrating the internal structure of the sanitary washing device according to the embodiment.

Figure 5:
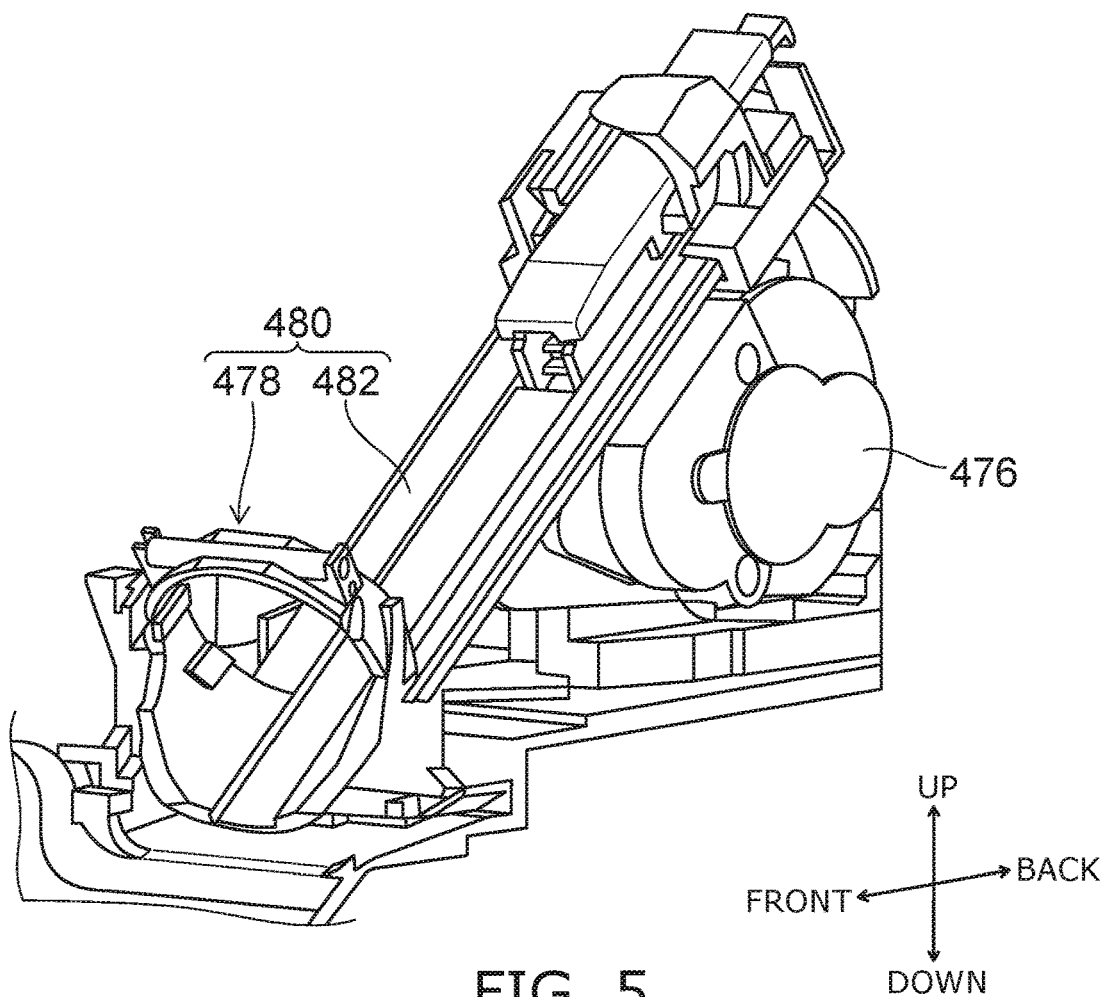
FIG. 5 is a perspective view illustrating the nozzle container of the sanitary washing device according to the embodiment.

FIG. 5 is a perspective view illustrating the nozzle container of the sanitary washing device according to the embodiment.

Figure 8A:
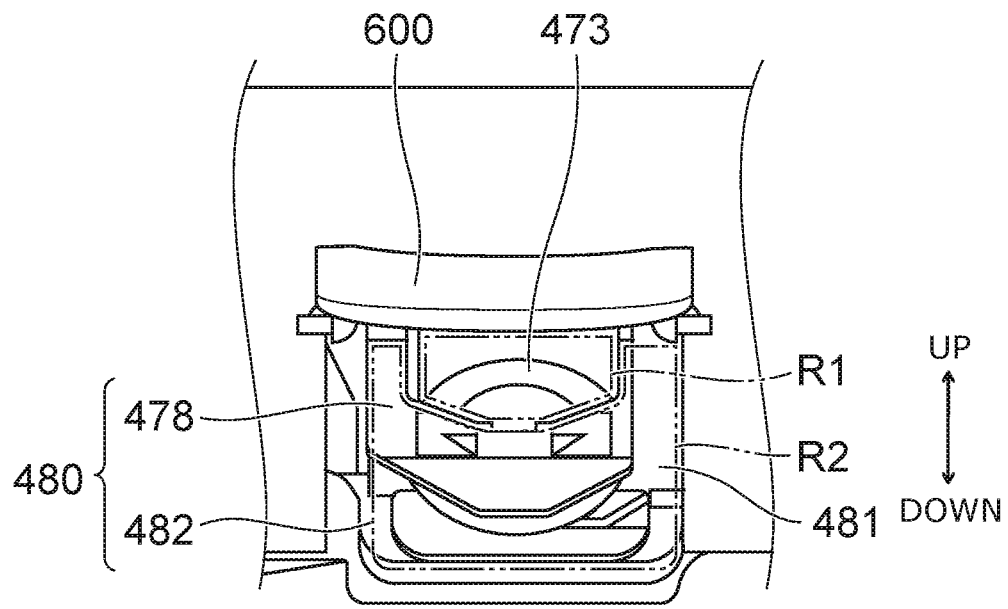
FIG. 8A and FIG. 8B are front views illustrating the private part wash nozzle periphery of the sanitary washing device according to the embodiment.
Figure 8B:
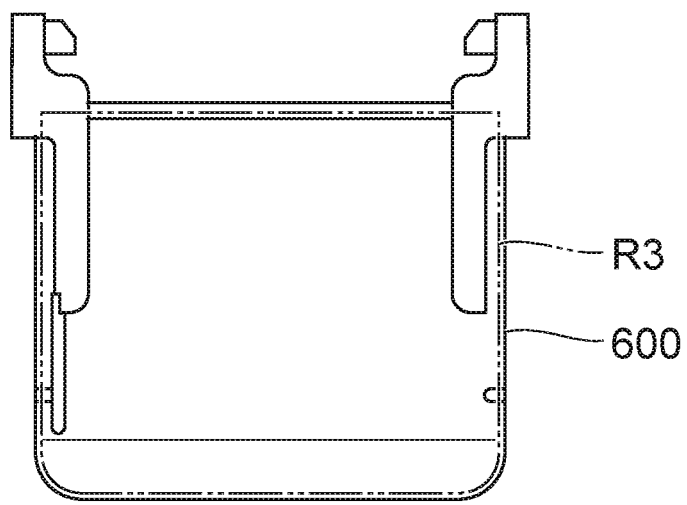

FIG. 8A and FIG. 8B are front views illustrating the private part wash nozzle periphery of the sanitary washing device according to the embodiment.

The configuration other than the nozzle 473 of the sanitary washing device 100 is not illustrated in FIG. 4.

Figure 3A:
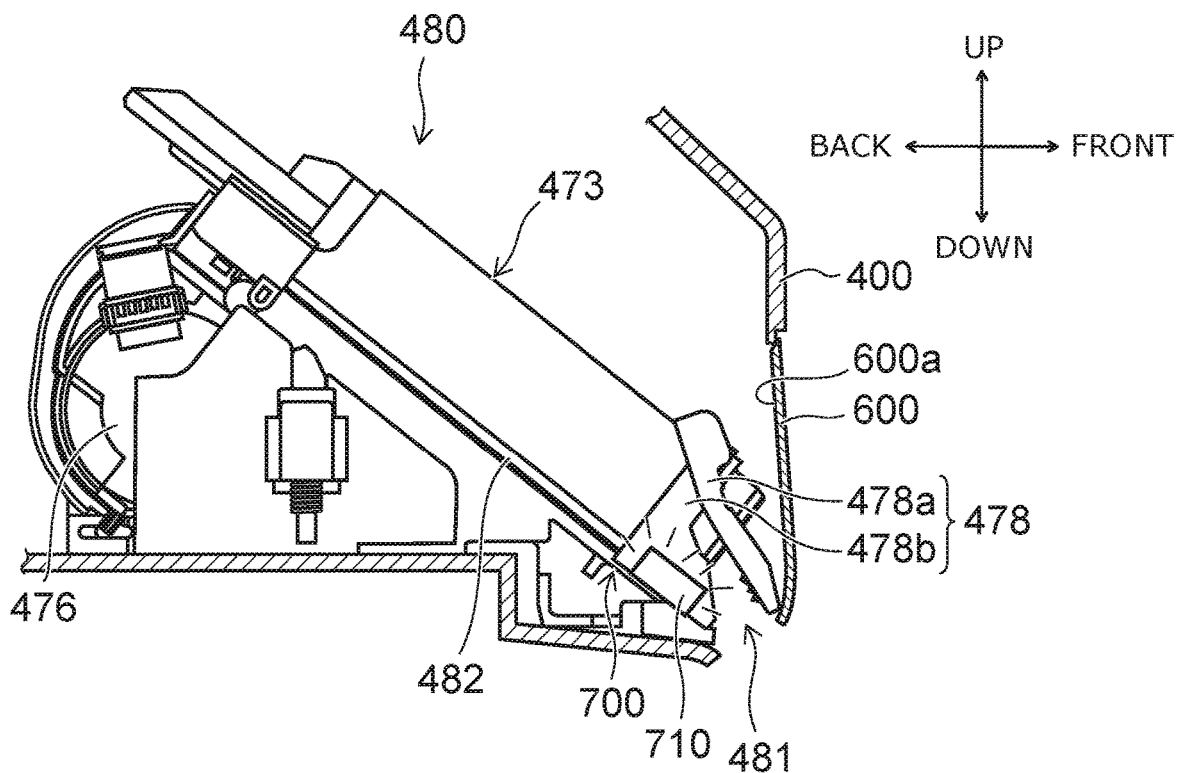
FIG. 3A and FIG. 3B are cross-sectional views illustrating the private part wash nozzle periphery of the sanitary washing device according to the embodiment.

As illustrated in FIG. 3A and FIG. 4, the casing 400 includes a nozzle container 480 that can store the entire nozzle 473 in the state in which the nozzle 473 is retracted. The nozzle container 480 is a member for storing the nozzle 473. The nozzle container 480 is adjacent to the nozzle 473 in the state in which the entire nozzle 473 is stored. In the example as illustrated in FIG. 5, a nozzle supporter 482 and the nozzle washer 478 are provided as the nozzle container 480.

The nozzle supporter 482 supports the nozzle 473 below the nozzle 473. The nozzle supporter 482 is tilted downward from the back toward the front. The nozzle 473 advances and retracts while sliding with respect to the nozzle supporter 482. For example, a tubular member that stores the nozzle 473 may be provided in the nozzle container 480.

The nozzle washer 478 is mounted to the front end of the nozzle supporter 482. As illustrated in FIG. 3A, the nozzle washer 478 includes a water discharger 478a in which water discharge holes discharging washing water are formed, and a support body 478b of the water discharger 478a. As illustrated in FIG. 3A and FIGS. 8A and 8B, an opening 481 is provided at the lower part of the front end of the casing 400. The nozzle washer 478 is positioned backward of the opening 481. For example, the nozzle washer 478 washes the outer perimeter surface (the central body) of the nozzle 473 (self-cleaning) by squirting water or functional water from the water discharger 478a when the nozzle 473 advance and retracts.

Figure 3B:
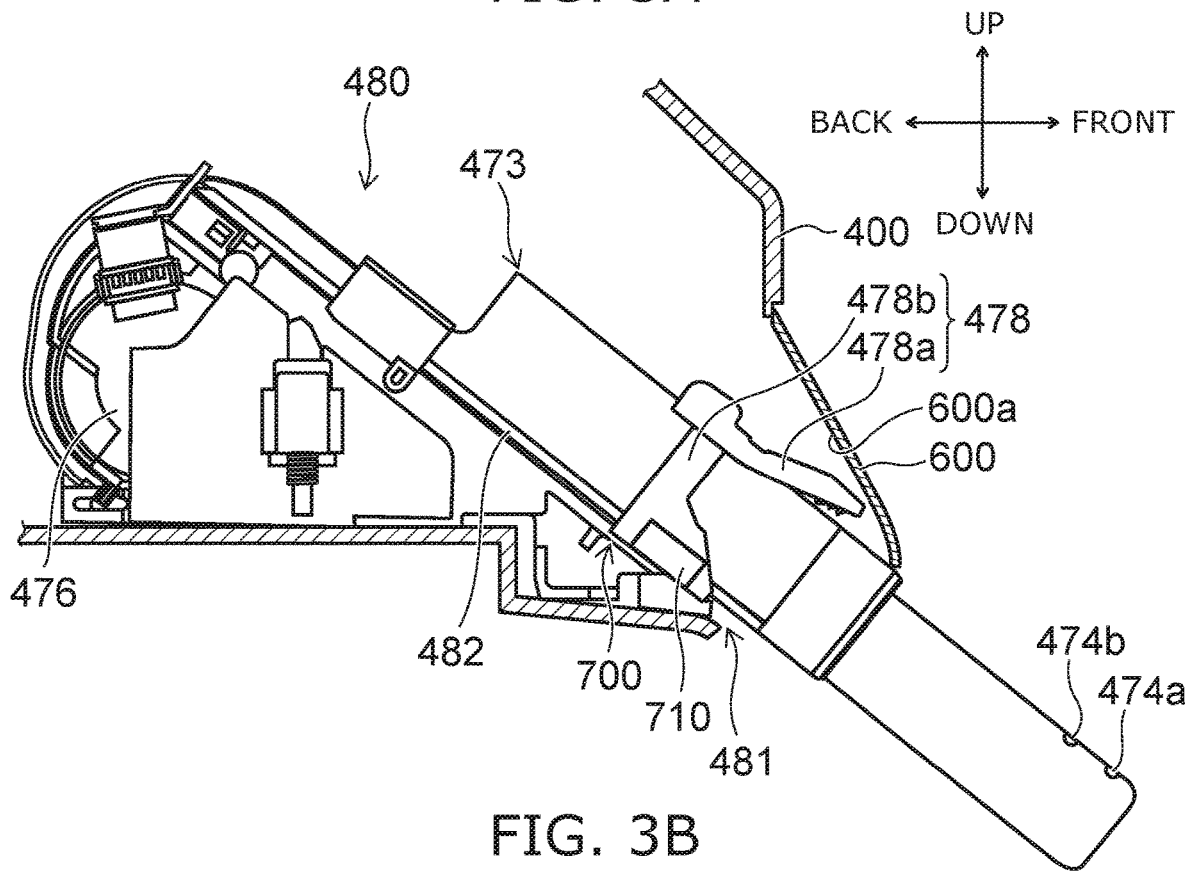

A nozzle lid 600 is provided at the front of the nozzle 473 and the nozzle washer 478. The nozzle lid 600 is provided to be openable and closable with respect to the opening 481. As illustrated in FIG. 3B, the nozzle lid 600 is in the open state in which the opening 481 is open when the nozzle 473 is advanced. As illustrated in FIG. 3A, the nozzle lid 600 is in the closed state in which the opening 481 is closed when the entire nozzle 473 is stored in the nozzle container 480. For example, when the nozzle lid 600 is in the closed state, the opening 481 that is provided in the front end of the nozzle container 480 is sealed with the nozzle lid 600.

In the state in which the nozzle 473 is not used, the nozzle 473 is stored in the nozzle container 480 as illustrated in FIG. 3A. When the private part wash is performed by the nozzle 473, the nozzle 473 slides frontward and downward with respect to the nozzle container 480. When the nozzle 473 slides frontward and downward, the nozzle 473 contacts the nozzle washer 478; and the nozzle lid 600 and the water discharger 478a of the nozzle washer 478 are pushed upward. For example, the nozzle 473 is washed by discharging water from the water discharger 478a until the nozzle 473 reaches a prescribed position.

When the nozzle 473 reaches a prescribed position as illustrated in FIG. 3B, water is discharged from the bidet wash water discharge port 474a or the bottom wash water discharge port 474b toward the private part of the user; and washing is performed. When the private part wash is completed, the nozzle 473 slides backward and upward toward the nozzle container 480. For example, the nozzle 473 is washed by discharging water from the water discharger 478a until the nozzle 473 is stored in the nozzle container 480. The nozzle 473 retracts to a prescribed position and is stored in the nozzle container 480 as in the state illustrated in FIG. 3A.

Figure 6:
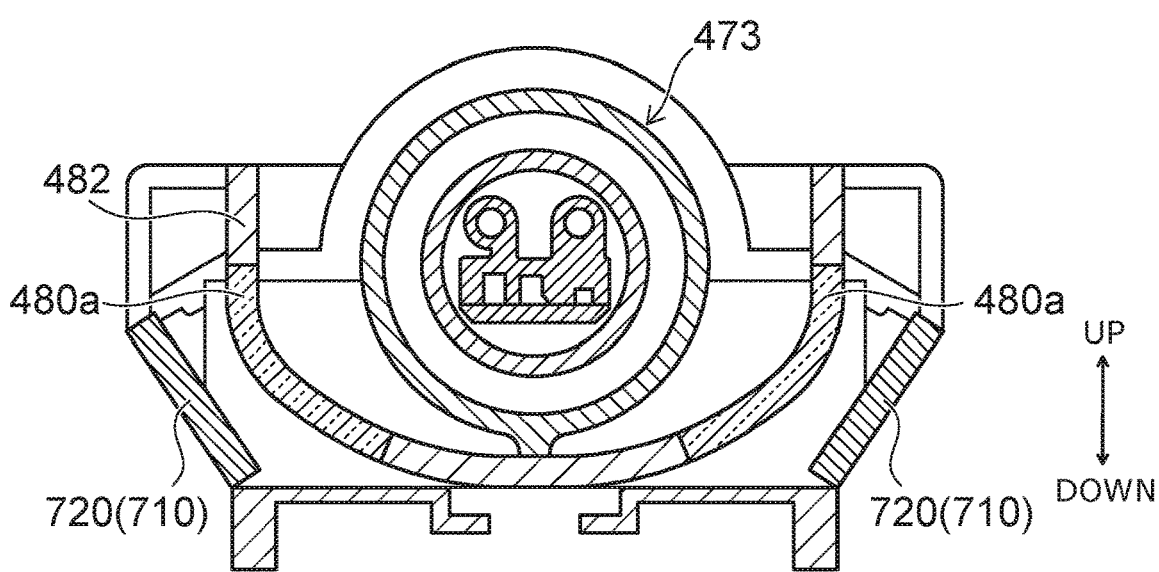
FIG. 6, FIG. 7A, and FIG. 7B are cross-sectional views illustrating the private part wash nozzle periphery of the sanitary washing device according to the embodiment.

As illustrated in FIG. 3A, FIG. 3B, FIG. 4, and FIG. 6, the sanitary washing device 100 includes the illuminator 700. The illuminator 700 irradiates sterilizing light which is light having a sterilizing action. By the irradiation of the sterilizing light, at least a part of the bacteria adhered to the object is sterilized by being annihilated or deactivated. The wavelength of the sterilizing light is 250 nm to 480 nm. As a result of investigations by the inventors, it was found that sterilizing light of a wavelength in the vicinity of 250 nm to 300 nm can reprogram the DNA to sterilize bacteria, mold, etc., so that bacteria, mold, etc., cannot proliferate. It was found that sterilizing light of a wavelength in the vicinity of 300 to 480 nm sterilizes by acting on the moisture inside the body of bacteria, mold, etc., to produce radicals and annihilate or deactivate the bacteria. The inventors confirmed that hydrogen peroxide is produced inside service water by irradiating a wavelength of 300 nm to 480 nm on the service water. This means that hydrogen peroxide is produced inside the water in the process of radical production. The inventors confirmed that bacteria inside water can be sterilized by irradiating light of a wavelength of 300 nm to 480 nm on the bacteria inside the water. For example, the illuminator 700 is provided in the interior of the casing 400. In the example as illustrated in FIG. 4 and FIG. 6, the illuminator 700 includes two light emitters 710. The two light emitters 710 are provided respectively at the side parts of the nozzle supporter 482 at the lower left and right.

The illuminator 700 includes, for example, a light-emitting element 720 (a light-emitting body). For example, the light-emitting element 720 is an LED (Light Emitting Diode). The light-emitting element 720 is not limited to an LED and may be, for example, a LD (Laser Diode), an OLED (Organic Light Emitting Diode), etc. A cold cathode fluorescent tube or a hot cathode fluorescent tube may be used instead of the light-emitting element. For example, the light-emitting element 720 is connected to the controller 405 shown in FIG. 2 via a substrate and is switched ON and switched OFF based on a control of the controller 405. The controller 405 controls the operation of the illuminator 700 by controlling the ON and OFF of the light-emitting element 720. The controller 405 may control the total luminous flux of the light-emitting element 720 by, for example, adjusting the voltage applied to the light-emitting element 720. For example, the light-emitting element 720 is provided in the light emitter 710.

The light emitter 710 irradiates the sterilizing light toward the front sides (the opening 481 sides) of the nozzle 473 and the nozzle container 480. The visible region that includes the front surface of the nozzle 473 and the part of the nozzle container 480 positioned below the nozzle 473 are sterilized by the sterilizing light.

Figure 7A:
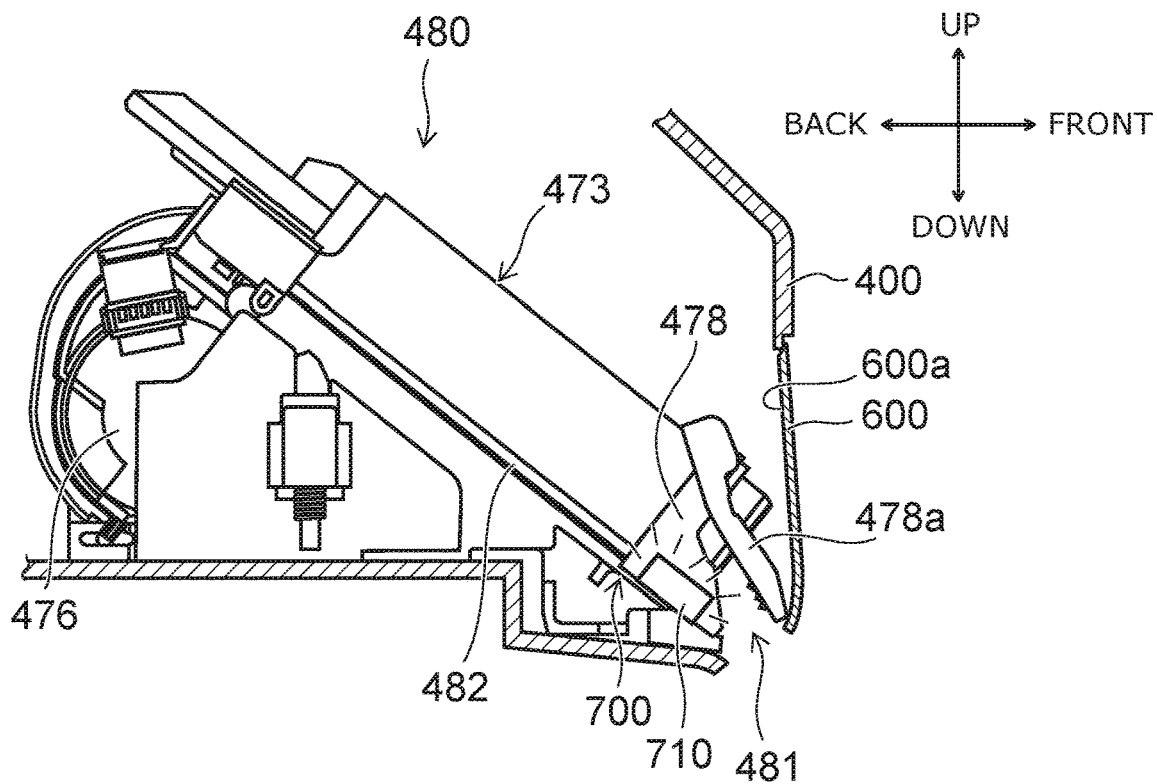
Figure 7B:
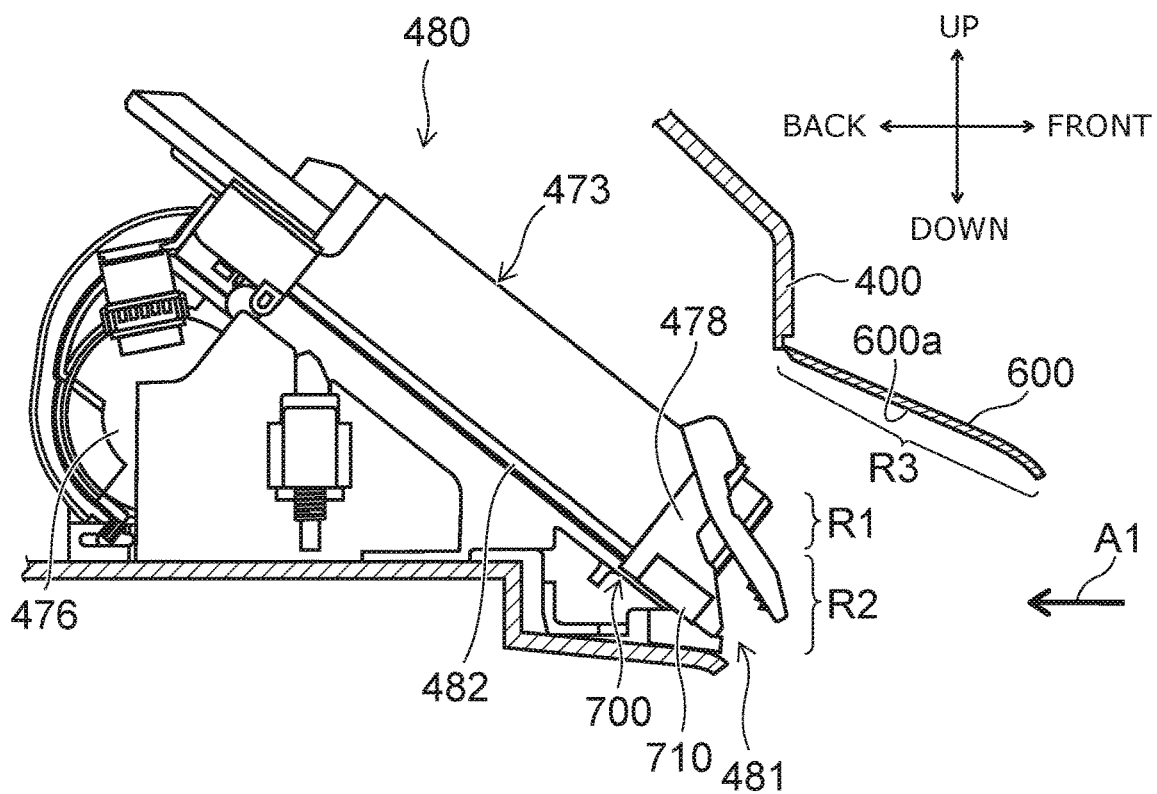

The visible region is described more specifically with reference to FIG. 7A, FIG. 7B, FIG. 8A, and FIG. 8B. FIG. 7A illustrates the state in which the entire nozzle 473 is stored in the nozzle container 480. FIG. 7B illustrates the state in which the user has fully opened the nozzle lid 600. The visible region refers to the front surface of the nozzle 473 and the part of the nozzle container 480 positioned below the nozzle 473. These parts cannot be visually confirmed by the user in the state illustrated in FIG. 7A, but are visible to the user in the state illustrated in FIG. 7B. For example, the visible region is a region R1 of the front surface of the nozzle 473 and a region R2 of the nozzle container 480 that are visible when the user views the sanitary washing device 100 in the direction illustrated by arrow A1 in the state illustrated in FIG. 7B.

The adhesion of dirt to the sections visible when the user opens the nozzle lid 600 can be suppressed by providing the illuminator 700 irradiating the sterilizing light on the visible region. In particular, according to the sanitary washing device 100 according to the invention, the sterilizing light is irradiated also on the front surface of the nozzle 473, the part of the nozzle container 480 positioned below the nozzle 473, etc., such as the region R1 and the region R2 illustrated in FIG. 7B. These parts are easily viewed by the user when the nozzle lid 600 is open. On the other hand, in the normal irradiation of the sterilizing light on the nozzle 473, it is difficult to irradiate the sterilizing light sufficiently on these parts. According to the invention, the user can be caused to perceive that the nozzle 473 is stored at a clean location because the adhesion of the dirt can be suppressed by irradiating the sterilizing light also on these parts. Therefore, even a highly cleanliness-conscious user can use the nozzle 473 with peace of mind.

It is desirable for the illuminator 700 to irradiate the sterilizing light on the entire visible region. In this specification, "irradiating the sterilizing light on the entire visible region" refers to irradiating sterilizing light on 50% or more of the visible region, and favorably 70% or more of the visible region, and more favorably 90% or more of the visible region with an illuminance such that the bacteria has a 99% decrease when irradiated for 24 hours. The entire visible region is substantially sterilized by the illuminator 700.

The visible region may further include a region that is visible when the user uses a hand mirror, etc., in the state illustrated in FIG. 7B. For example, as illustrated in FIG. 7B and FIG. 8B, a region R3 may be included in the visible region in addition to the regions R1 and R2. The regions R1 and R2 are regions that are directly visible to the naked eye in the direction of arrow A1 in the state in which the nozzle lid 600 is fully open. The region R3 is a region of a back surface 600a of the nozzle lid 600 that is visible when using a hand mirror, etc. In other words, the illuminator 700 irradiates the sterilizing light L also on the back surface 600a in addition to the regions R1 and R2.

This is because a highly cleanliness-conscious user may use a hand mirror or the like to confirm regions that cannot be directly viewed with the naked eye while cleaning the sanitary washing device 100. The adhesion of dirt to the back surface 600a can be suppressed by irradiating the sterilizing light L also on the back surface 600a. Therefore, even a user that views the back surface 600a can be caused to perceive that the nozzle 473 is stored at a clean location. The user can use the nozzle 473 with peace of mind.

The illuminator 700 irradiates the sterilizing light with more particular emphasis on the visible region than on the non-visible region. The non-visible region is the region inside the nozzle container 480 other than the visible region. For example, the illuminator 700 is configured to cause the average illuminance of the sterilizing light in the visible region to be larger than the average illuminance of the sterilizing light in the non-visible region. Or, the illuminator 700 is configured to cause the irradiation area of the sterilizing light in the visible region to be wider than the irradiation area of the sterilizing light in the non-visible region.

Thereby, the dirt removal performance in the visible region where high cleanliness is necessary can be high. In recent years, it has become desirable to downsize the sanitary washing device 100 to improve the designability. By irradiating the sterilizing light with more particular emphasis on the visible region than on the non-visible region, the unnecessary irradiation of the sterilizing light can be suppressed; and the electrical power that is applied to the illuminator 700 can be reduced. The heat generation of the illuminator 700 decreases as the electrical power decreases. Thereby, the heat sink that dissipates the heat of the illuminator 700, etc., can be small; and the illuminator 700 can be downsized. As a result, the sanitary washing device 100 can be downsized.

The average illuminance of the sterilizing light in the visible region is calculated by averaging the illuminance of the sterilizing light at each point of the visible region. The average illuminance of the sterilizing light in the non-visible region is calculated by averaging the illuminance of the sterilizing light at each point of the non-visible region.

The irradiation area of the sterilizing light in the visible region is represented by the surface area of the part of the visible region where the sterilizing light having not less than a prescribed illuminance is irradiated. The irradiation area of the sterilizing light in the non-visible region is represented by the surface area of the part of the non-visible region where the sterilizing light having not less than the prescribed illuminance is irradiated. The prescribed illuminance is, for example, 5 mW/cm$^2$.

It is desirable for the non-visible region of the nozzle container 480 to be formed to guide the water in the non-visible region into the visible region of the nozzle container 480. The water in the non-visible region is due to the private part wash, the self-cleaning of the nozzle 473, etc. In the example illustrated in FIGS. 3A and 3B and FIG. 5, the nozzle supporter 482 that is included in the nozzle container 480 is tilted downward from the back toward the front. In other words, the non-visible region is formed so that the water is guided from the back side of the nozzle supporter 482 which is the non-visible region to the front side of the nozzle supporter 482 which is the visible region.

According to this configuration, the occurrence of remaining water that results in bacteria and mold proliferating in the non-visible region can be suppressed; and the adhesion of dirt in the non-visible region can be suppressed. As a result, the propagation of bacteria and mold in the visible region due to spores emitted into the nozzle container from mold occurring in the non-visible region can be suppressed.

For example, as described above, the light emitters 710 are provided at side parts below the nozzle supporter 482. Although the light emitters 710 may be provided inside the nozzle container 480, it is desirable for the light emitters 710 to be provided outside the nozzle container 480 as illustrated in FIG. 4 and FIG. 6. Water scatters inside the nozzle container 480 when the nozzle 473 is washed and when the washed nozzle 473 is stored. Accordingly, if the light emitters 710 is provided inside the nozzle container 480, water may contact the light emitters 710 and cause a malfunction of the light emitters 710. By providing the light emitters 710 outside the nozzle container 480, the water does not contact the light emitters 710 and the power supply parts of the light emitters 710; and the malfunction of the light emitters 710 can be prevented.

When the light emitters 710 are provided outside the nozzle container 480, it is desirable for the part of the nozzle container 480 where the sterilizing light is irradiated to be light-transmissive. In other words, it is desirable for the nozzle container 480 to include a transmissive part 480a (shown in FIG. 6) for guiding the sterilizing light emitted from the light emitters 710 into the nozzle container 480. By providing the transmissive part 480a, the illuminance of the sterilizing light irradiated in the visible region inside the nozzle container 480 can be increased; and the sterilizing action can be increased.

FIG. 9A to FIG. 9C are cross-sectional views illustrating examples of the private part wash nozzle periphery of the sanitary washing device according to the embodiment. The visible region where the sterilizing light is irradiated is marked with dots in FIG. 9A to FIG. 9C.

As illustrated in FIG. 9A, the illuminator 700 includes, for example, a reflector 740 for irradiating the sterilizing light L on the entire visible region. The reflector 740 reflects the sterilizing light L radiated from the light emitters 710 toward the visible region. For example, the reflector 740 is formed of a metal material to increase the reflectance. It is desirable to perform mirror finishing of the front surface of the reflector 740 (the surface opposing the light emitters 710). Or, the reflector 740 may be formed of a resin material having a high reflectance. For example, a fluoric compound or a compound of a polyester is used as such a resin material. The entire reflector 740 may include a material having a high reflectance such as that described above; or only a part of the reflector 740 may include the material having the high reflectance.

Or, the illuminator 700 may include a light guide part 750. As illustrated in FIG. 9B, the light guide part 750 is, for example, the nozzle washer 478 formed of a light guide material. By forming the nozzle washer 478 of the light guide material, the sterilizing light L that is irradiated on the nozzle washer 478 passes through the interior of the nozzle washer 478 and is radiated from the nozzle washer 478.

As illustrated in FIG. 9C, the light guide part 750 may be the nozzle lid 600 formed of a light guide material. By forming the nozzle lid 600 of the light guide material, the sterilizing light L that is irradiated on the nozzle lid 600 passes through the interior of the nozzle lid 600 and is radiated from the nozzle lid 600.

For example, an acrylic resin member, a silicon resin, glass, or the like is used as the light guide material included in the nozzle washer 478 or the nozzle lid 600.

By the illuminator 700 including the reflector 740 or the light guide part 750, the sterilizing light can be irradiated efficiently also on the front end surface of the nozzle 473 which is in a shadow, etc., from the light emitters 710. Thereby, the sterilizing light can be irradiated efficiently on the entire visible region by smaller (or fewer) light emitters 710; and the sanitary washing device 100 can be downsized.

The specific configuration of the illuminator 700 is modifiable as appropriate.

FIG. 10A to FIG. 10C are cross-sectional views illustrating other examples of the private part wash nozzle periphery of the sanitary washing device according to the embodiment. The visible region where the sterilizing light is irradiated is marked with dots in FIG. 10A to FIG. 10C.

Figure 11:
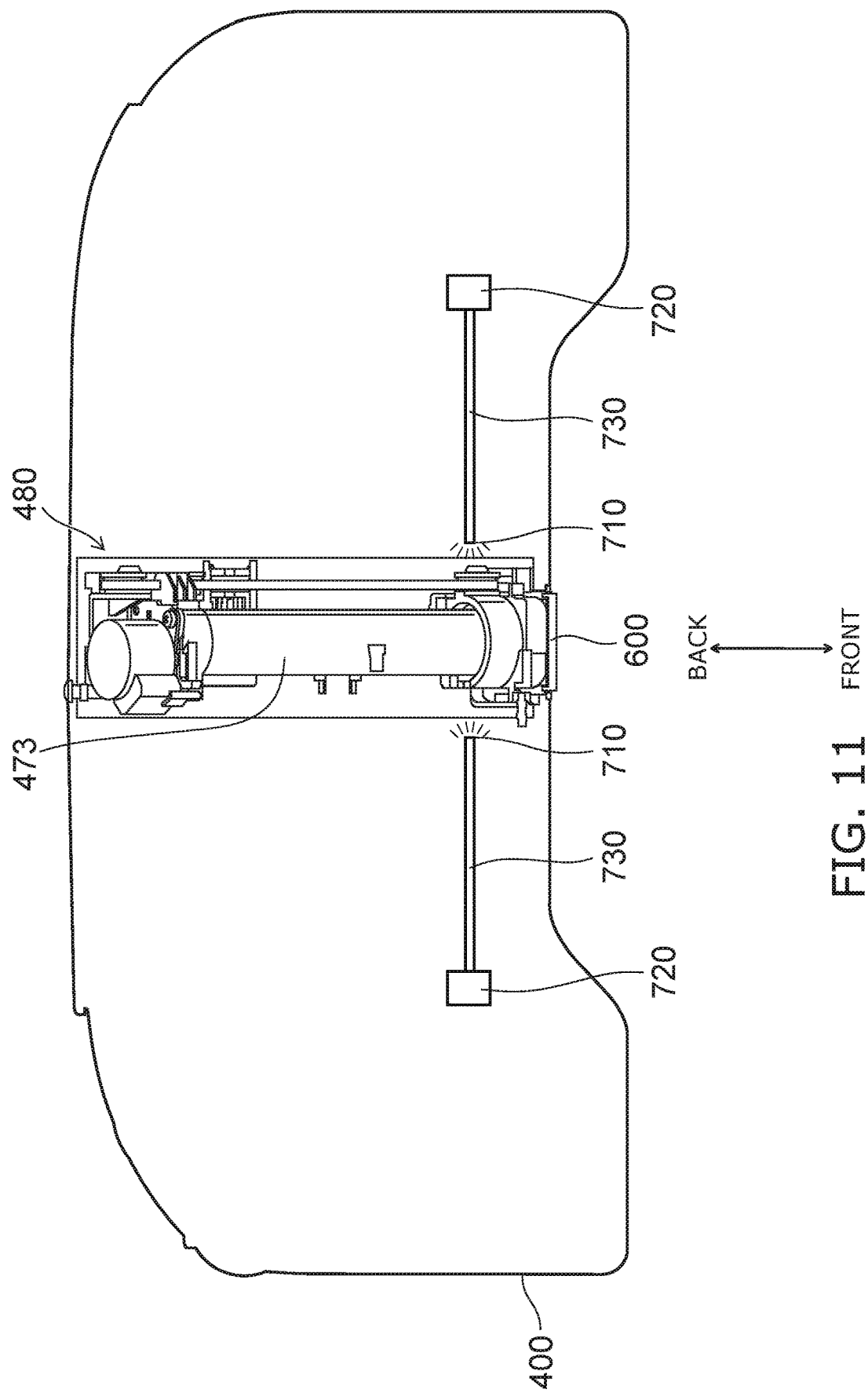
FIG. 11 is a plan view illustrating a modification of the illuminator of the sanitary washing device according to the embodiment.

FIG. 11 is a plan view illustrating a modification of the illuminator of the sanitary washing device according to the embodiment.

For example, as illustrated in FIG. 10A, the light emitter 710 may be provided above the front end of the nozzle 473. In the sanitary washing device 100, more space exists above the nozzle 473 than at the side or below the nozzle 473. Accordingly, by providing the light emitter 710 above the front end of the nozzle 473, the sanitary washing device 100 can be downsized compared to the case where the light emitter 710 is provided at the side or below the nozzle 473.

When the light emitter 710 is provided above the front end of the nozzle 473, the light emitter 710 irradiates the sterilizing light L downward. In such a case as well, it is desirable for the illuminator 700 to include the reflector 740 or the light guide part 750 as illustrated in FIG. 10A to FIG. 10C. By providing the reflector 740 or the light guide part 750, the sterilizing light L can be irradiated efficiently also on the front end surface of the nozzle 473 which is in a shadow, the nozzle container 480 positioned below the nozzle 473, etc., from the light emitter 710.

As illustrated in FIG. 11, the light-emitting element 720 may be provided at a position distal to the nozzle container 480. In the example, two light-emitting elements 720 are provided at positions distal to the nozzle container 480 respectively at the left and right. The two light-emitting elements 720 are connected respectively to two light emitters 710 provided at the side parts of the nozzle container 480 at the left and right via optical fibers 730.

Thus, in the embodiment, the sterilizing light may be guided from the light-emitting element 720 to the light emitter 710 by an optical fiber, etc.; and the sterilizing light may be irradiated on the nozzle container 480 from the light emitter 710 provided at the nozzle container 480 vicinity.

Figure 12:
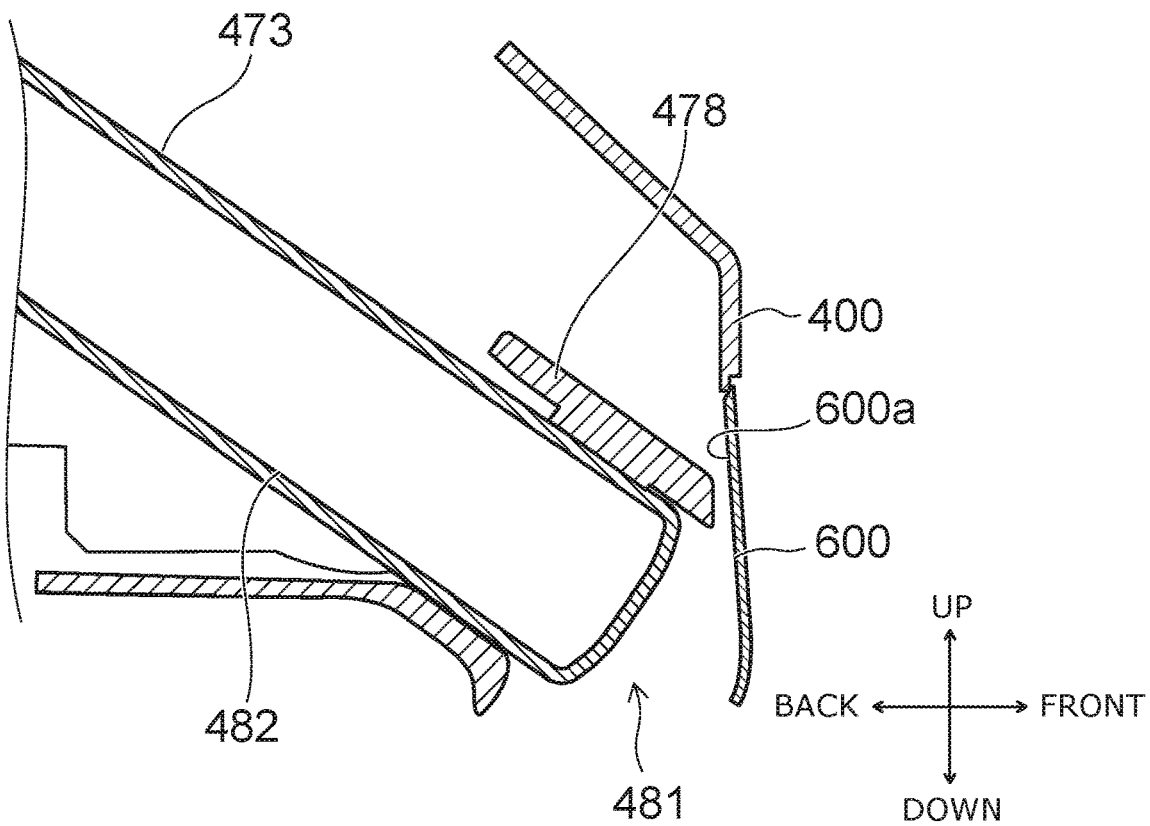
FIG. 12 is a cross-sectional view illustrating a modification of the nozzle washer of the sanitary washing device according to the embodiment.

FIG. 12 is a cross-sectional view illustrating a modification of the nozzle washer of the sanitary washing device according to the embodiment.

Figure 13:
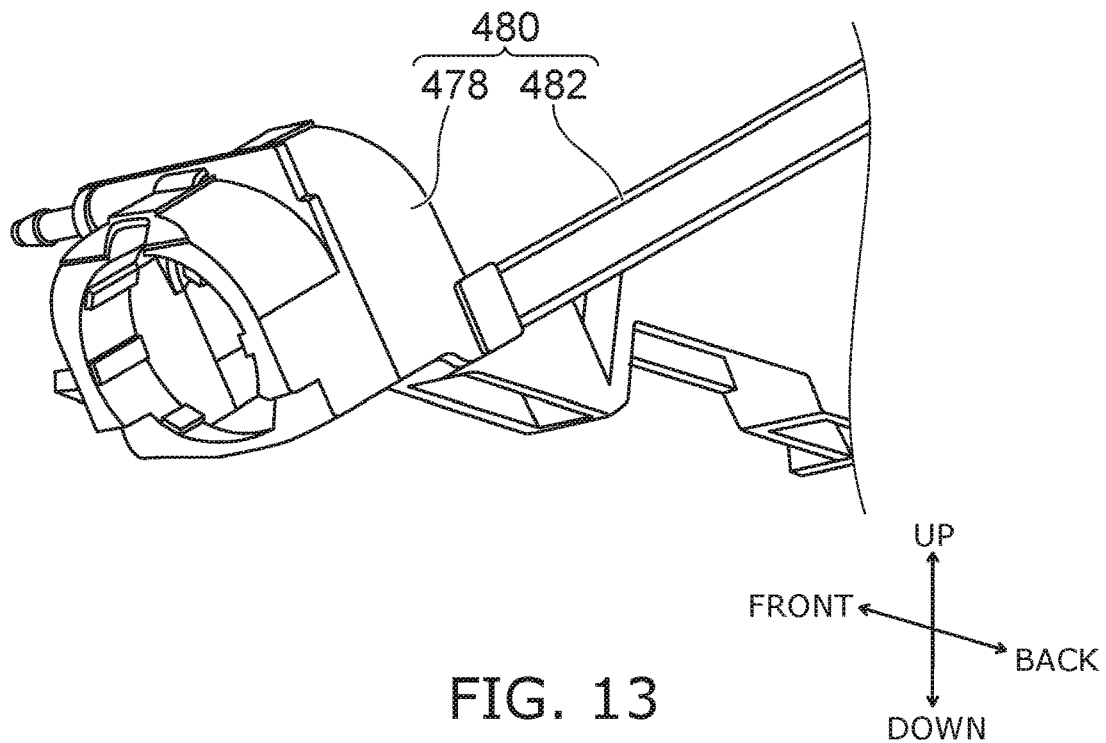
FIG. 13 is a perspective view illustrating the modification of the nozzle washer of the sanitary washing device according to the embodiment.

FIG. 13 is a perspective view illustrating the modification of the nozzle washer of the sanitary washing device according to the embodiment.

Figure 14:
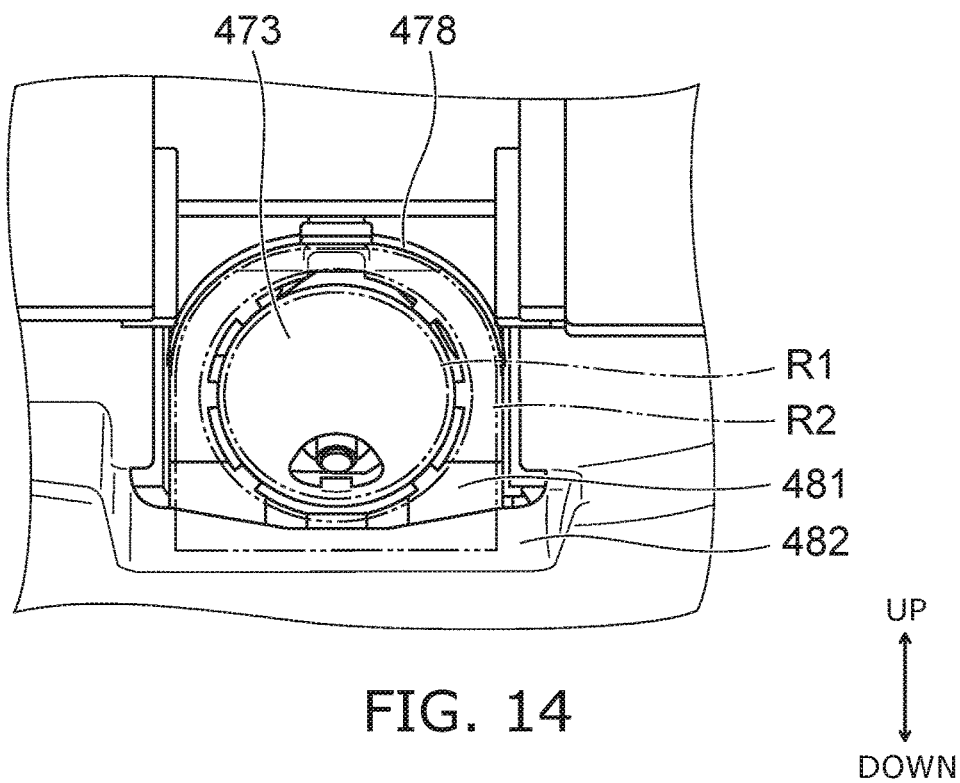
FIG. 14 is a front view illustrating the modification of the nozzle washer of the sanitary washing device according to the embodiment.

FIG. 14 is a front view illustrating the modification of the nozzle washer of the sanitary washing device according to the embodiment.

The structure of the nozzle washer 478 is not limited to the examples illustrated in FIGS. 3A and 3B and FIG. 5. For example, the nozzle washer 478 illustrated in FIG. 12 and FIG. 13 may be provided. In the example, the nozzle washer 478 is a tubular member mounted to the tip of the nozzle supporter 482. The front end of the nozzle 473 is surrounded with the nozzle washer 478 in the state in which the nozzle 473 is completely retracted. A water discharge hole for discharging washing water toward the outer perimeter of the nozzle 473 is formed in the inner wall of the nozzle washer 478. For example, the nozzle container 480 includes the nozzle washer 478 and the nozzle supporter 482.

Even when the nozzle washer 478 illustrated in FIG. 12 and FIG. 13 is provided, a visible region that is visible when the nozzle lid 600 is fully open exists in the sanitary washing device 100. For example, as illustrated in FIG. 14, the region R1 of the front surface of the nozzle 473 and the region R2 of the nozzle container 480 positioned below the nozzle 473 are the visible region. The illuminator 700 irradiates the sterilizing light in the visible region.

Thus, the structure of the nozzle container 480 vicinity is modifiable as appropriate. For any structure, the adhesion of dirt in the visible region of the front surface of the nozzle 473 and the part of the nozzle container 480 positioned below the nozzle 473 can be suppressed by irradiating the sterilizing light in the region.

Figure 15:
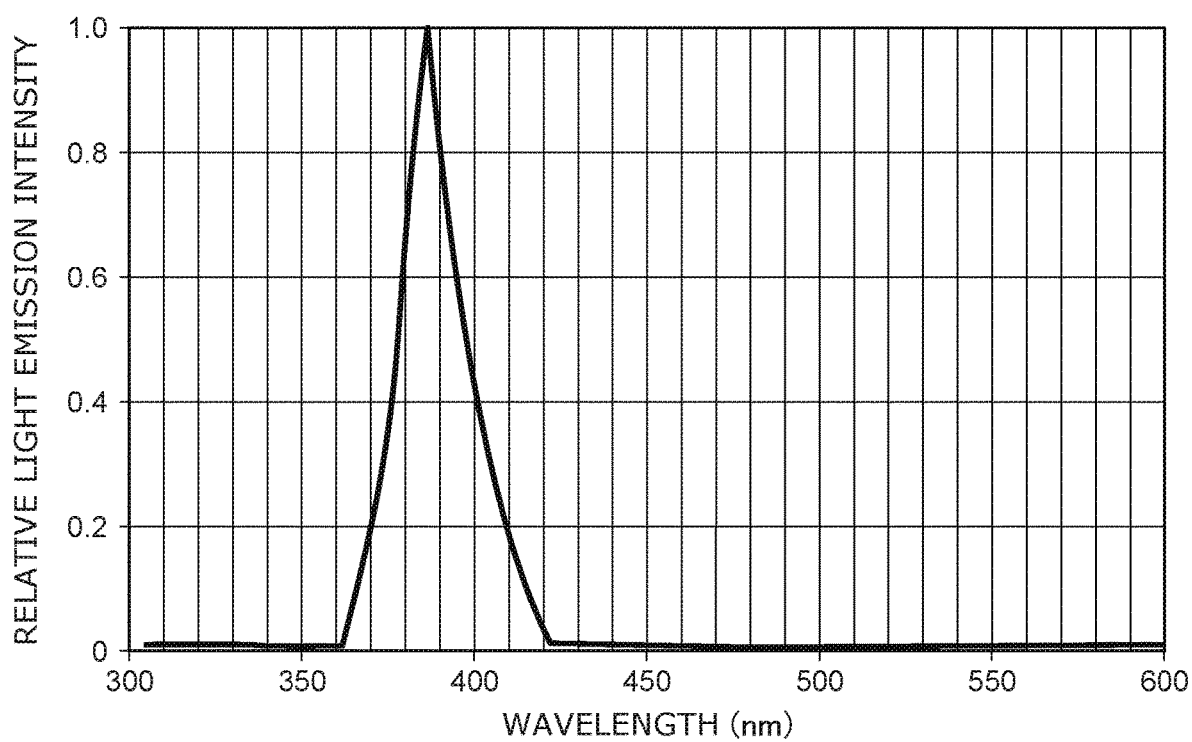
FIG. 15 is a graph illustrating an example of the wavelength distribution of the sterilizing light of the sanitary washing device according to the embodiment.

FIG. 15 is a graph illustrating an example of the wavelength distribution of the sterilizing light of the sanitary washing device according to the embodiment.

In the example as illustrated in FIG. 15, the sterilizing light includes light of a wavelength of about 360 nm to about 420 nm; and the peak wavelength is about 385 nm. Thus, by setting the peak wavelength of the sterilizing light at the boundary vicinity between the visible region and the ultraviolet region, for example, the sterilizing light that includes a UV-A component (not less than 315 nm and not more than 400 nm) which is the ultraviolet light component and a violet-to-blue visible light component (not less than 400 nm and not more than 480 nm) can be irradiated. Using such sterilizing light, both the sterilization effect of the nozzle container 480 by the sterilizing light and the visual confirmation effect by the user can be realized.

The number of light sources of the sterilizing light is not limited to one. For example, as the sterilizing light, light that includes an ultraviolet light component but does not include a visible light component may be irradiated from one light source, and light that includes a visible light component but does not include an ultraviolet light component may be irradiated from another light source. In other words, the ultraviolet light component and the visible light component included in the sterilizing light may be irradiated simultaneously from different light sources.

The sterilizing light is not limited to light including an ultraviolet light component and a visible light component. For example, when the nozzle lid 600 includes a wavelength conversion material, the sterilizing light may be light that includes an ultraviolet light component but does not include a visible light component.

A specific example of the operation of the sanitary washing device according to the embodiment will now be described with reference to the drawings.

Figure 16:
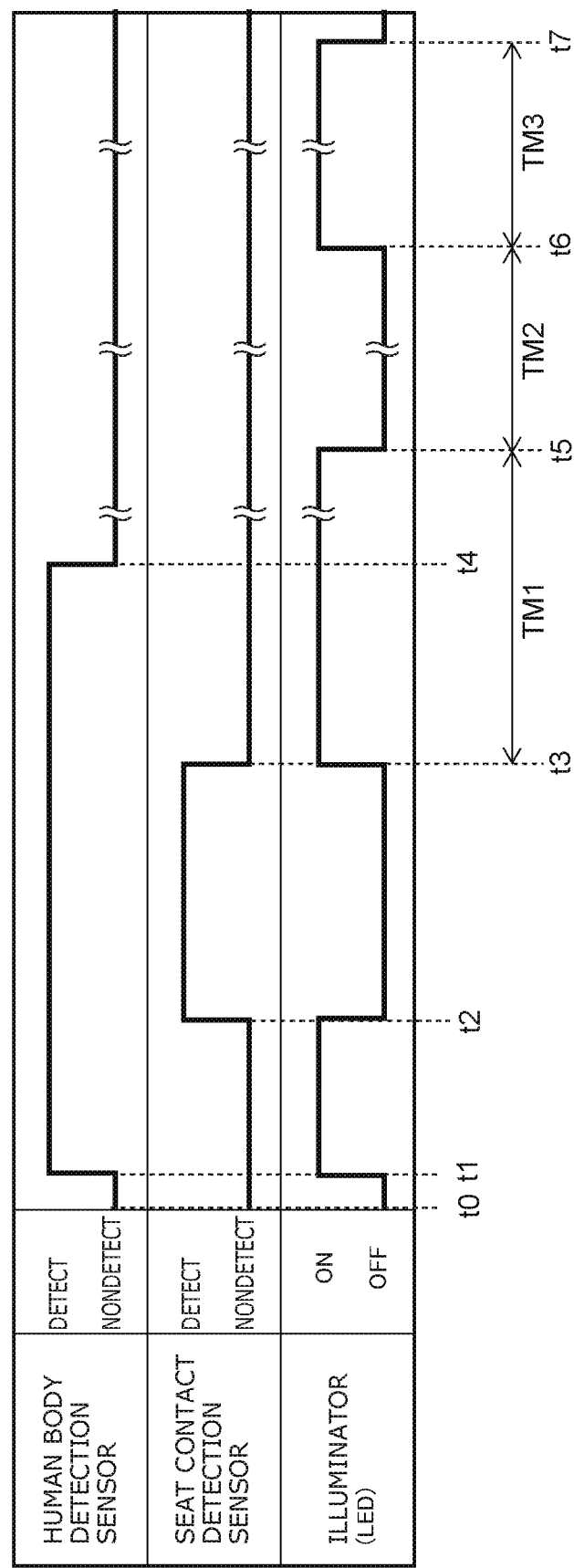
FIG. 16 is a timing chart illustrating the specific example of the operation of the sanitary washing device according to the embodiment.

FIG. 16 is a timing chart illustrating the specific example of the operation of the sanitary washing device according to the embodiment.

As illustrated in FIG. 16, the illuminator 700 does not operate in the state in which the human body detection sensor 403 does not detect the user (a timing t0). More specifically, the light-emitting element 720 of the illuminator 700 (e.g., the LED) is switched OFF (OFF).

When the human body detection sensor 403 detects the user approaching the sanitary washing device 100, the controller 405 operates the illuminator 700 (a timing t1). More specifically, the controller 405 switches ON the light-emitting element 720 of the illuminator 700 (ON).

Thus, the illuminator 700 is operated at the timing of detecting the user approaching the sanitary washing device 100. Thereby, the user can be caused to perceive that the nozzle container 480 is being sterilized by the sterilizing lighted before the user is seated on the toilet seat 200.

For example, the illuminator 700 continues to operate until the seat contact detection sensor 404 detects the seat contact of the user. In other words, the controller 405 continues to operate the illuminator 700 in the state in which the human body detection sensor 403 has detected the user but the seat contact detection sensor 404 has not detected the seat contact.

When the seat contact detection sensor 404 detects the seat contact of the user, the controller 405 stops the operation of the illuminator 700 (a timing t2). More specifically, the controller 405 switches OFF the light-emitting element 720 of the illuminator 700 (OFF).

After the user is seated on the toilet seat 200, a part of the sterilizing light easily may be irradiated on the user if the sterilizing light leaks outside the casing 400 from the opening 481. By stopping the operation of the illuminator 700 at the timing of the user being seated on the toilet seat 200, the irradiation of the sterilizing light on the user can be suppressed; and the safety of the user can be increased further.

For example, the illuminator 700 continues to stop the operation until the seat contact detection sensor 404 detects the user rising from the seat. In other words, the controller 405 continues to stop the operation of the illuminator 700 in the state in which the seat contact detection sensor 404 detects the seat contact.

The controller 405 operates the illuminator 700 when the seat contact detection sensor 404 detects the user rising from the seat (a timing t3). The detection by the seat contact detection sensor 404 of the user rising from the seat corresponds to switching from the state in which the seat contact detection sensor 404 detects the seat contact to the state in which the seat contact is not detected. More specifically, the controller 405 switches ON the light-emitting element 720 of the illuminator 700 (ON). Thereby, the user that has risen from the seat can be caused to perceive that the sterilization of the nozzle container 480 has restarted.

The illuminator 700 continues to operate until a prescribed period of time TM1 has elapsed. In other words, even when the state in which the human body detection sensor 403 detects the user changes to the state in which the user is not detected (a timing t4), the controller 405 continues to operate the illuminator 700 until the prescribed period of time TM1 has elapsed.

When the prescribed period of time TM1 has elapsed, the controller 405 stops the operation of the illuminator 700 (a timing t5). More specifically, the controller 405 switches OFF the light-emitting element 720 of the illuminator 700 (OFF).

The illuminator 700 is operated when a prescribed period of time TM2 has elapsed in the state in which the toilet device is unused. In other words, the controller 405 operates the illuminator 700 when the prescribed period of time TM2 has elapsed in the state in which the human body detection sensor 403 does not detect the user and the seat contact detection sensor 404 does not detect the seat contact (a timing t6). More specifically, the controller 405 switches ON the light-emitting element 720 of the illuminator 700 (ON). Thus, the controller 405 may operate the illuminator 700 in the state in which the human body detection sensor 403 does not detect the user.

The irradiation time of the sterilizing light can be lengthened by sterilizing the nozzle container 480 with the sterilizing light even in the state in which the human body detection sensor 403 does not detect the user. The sterilization effect of the nozzle container 480 due to the sterilizing light can be increased thereby. Even when the sterilizing light having a relatively long peak wavelength is irradiated, the decrease of the sterilization effect of the nozzle container 480 due to the sterilizing light can be suppressed by lengthening the irradiation time of the sterilizing light. Accordingly, the safety of the user can be increased while suppressing the decrease of the sterilization effect.

The controller 405 stops the operation of the illuminator 700 when a prescribed period of time TM3 has elapsed (a timing t7). More specifically, the controller 405 switches OFF the light-emitting element 720 of the illuminator 700 (OFF).

The prescribed periods of time TM1 to TM3 may be any time. For example, the prescribed periods of time TM1 to TM3 are set so that the operation time of the illuminator 700 in the state in which the human body detection sensor 403 does not detect the user is longer than the operation time of the illuminator 700 in the state in which the human body detection sensor 403 detects the user. In other words, for example, the controller 405 controls the illuminator 700 so that the operation time of the illuminator 700 in the state in which the human body detection sensor 403 does not detect the user is longer than the operation time of the illuminator 700 in the state in which the human body detection sensor 403 detects the user. The sterilization effect of the nozzle container 480 due to the sterilizing light can be increased further thereby.

Other Embodiment

FIG. 17 to FIG. 19B are cross-sectional views illustrating the private part wash nozzle periphery of a sanitary washing device according to another embodiment.

Figure 17:
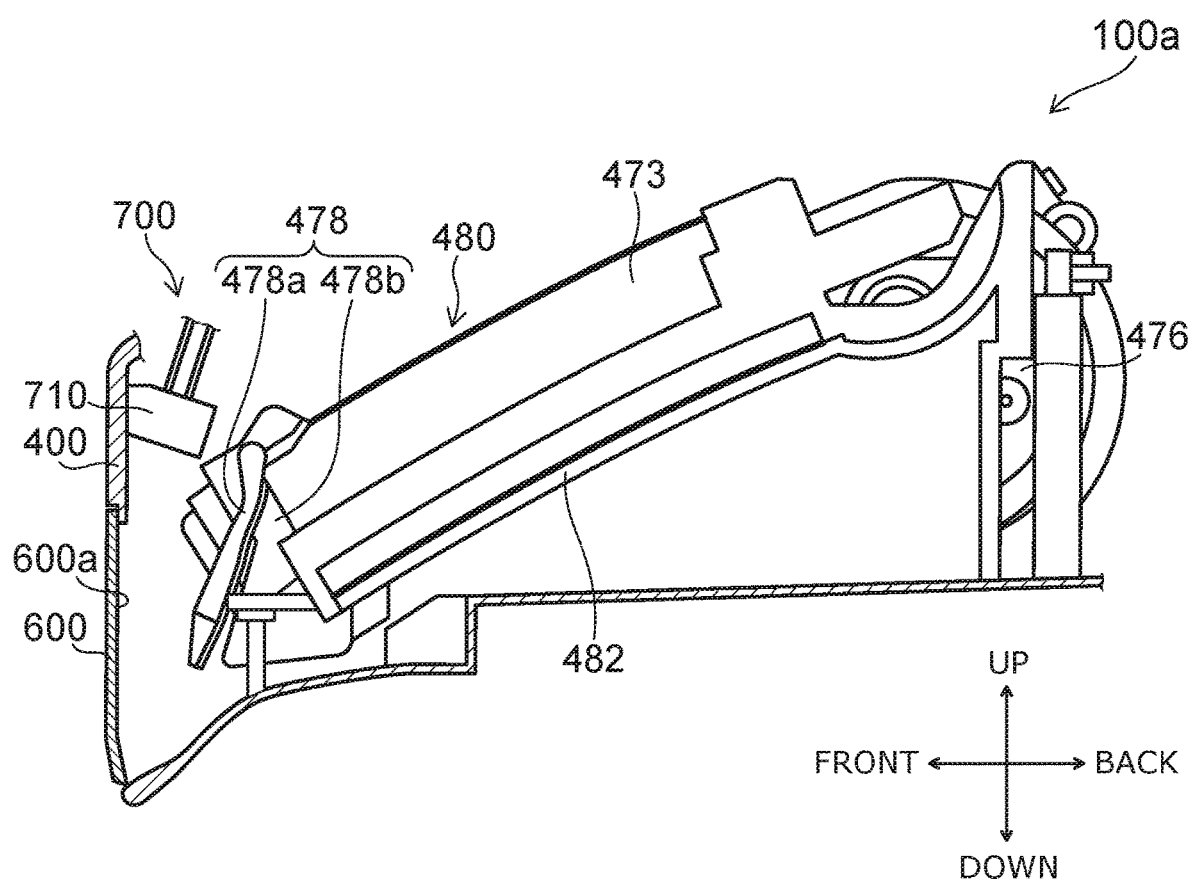
FIG. 17 to FIG. 19B are cross-sectional views illustrating the private part wash nozzle periphery of a sanitary washing device according to another embodiment.

In the sanitary washing device 100*a* according to the other embodiment as illustrated in FIG. 17, the light emitter 710 of the illuminator 700 is provided above the nozzle 473 and the nozzle lid 600.

Figure 18:
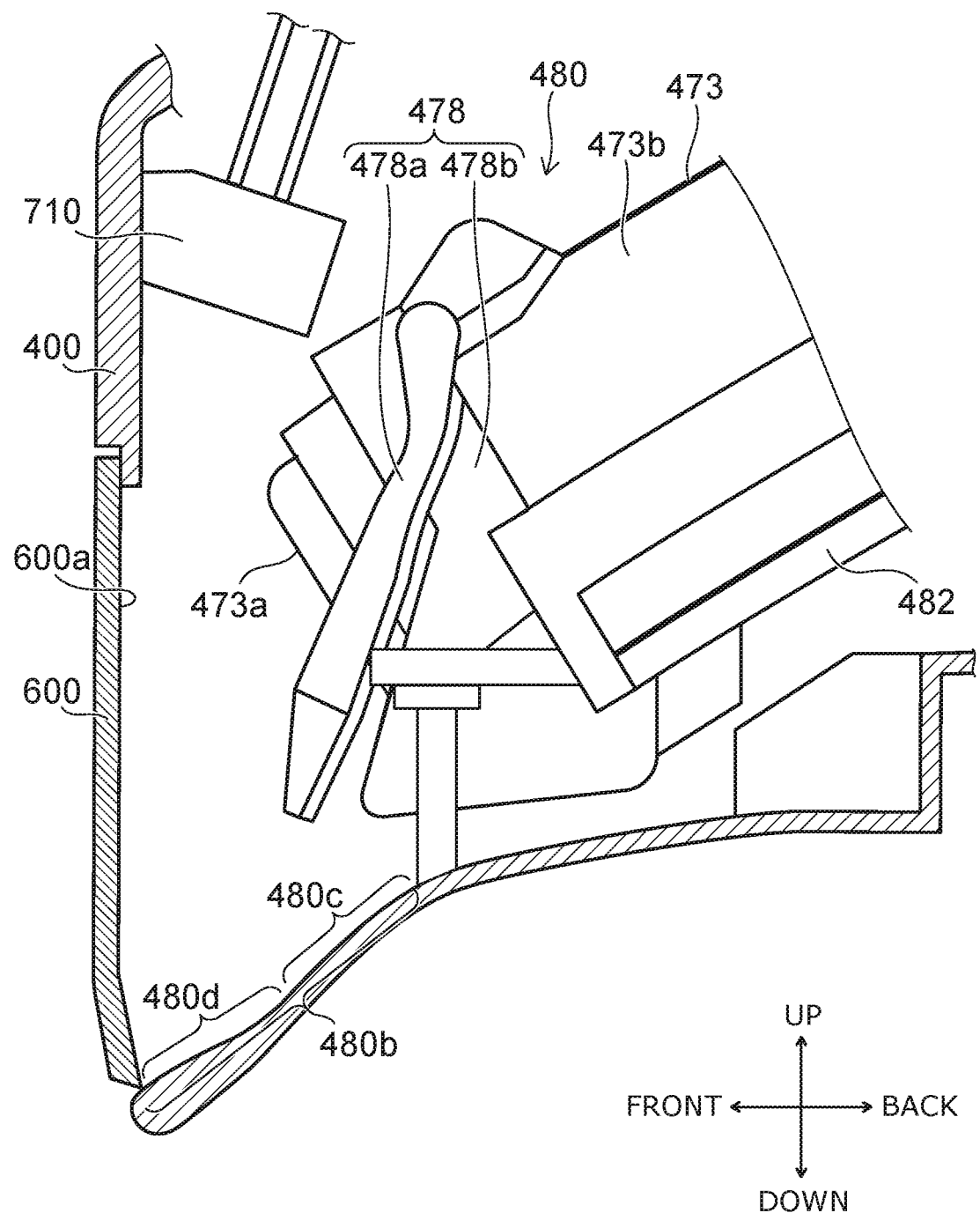
Figure 19A:
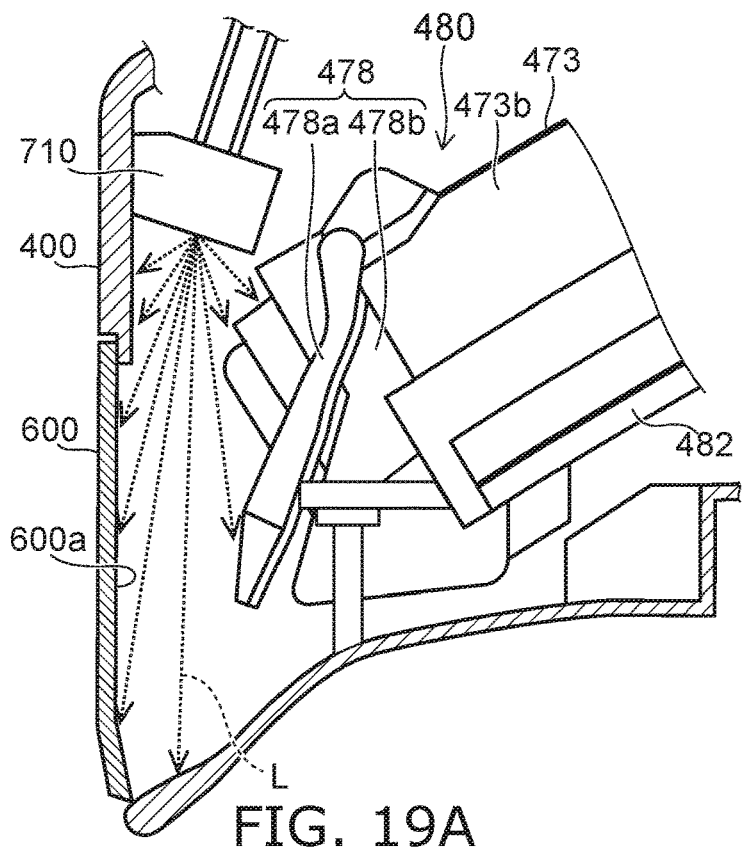

As illustrated in FIG. 18, the nozzle container 480 includes a bottom surface part 480*b*. The bottom surface part 480*b* is a part of the inner surface of the casing 400 and is positioned frontward of the nozzle supporter 482. The light emitter 710 irradiates the sterilizing light L downward as illustrated in FIG. 19A. Thereby, the sterilizing light L is irradiated on the back surface 600*a* of the nozzle lid 600, a part of the bottom surface part 480*b*, the upper surface of the nozzle 473, etc.

As illustrated in FIG. 18, the nozzle 473 has a front surface 473*a*. The front surface 473*a* is the surface positioned at the front of the nozzle 473 when the advance direction of the nozzle 473 is taken as the front. For example, the front surface 473*a* is substantially perpendicular to the advance direction of the nozzle 473. The bottom surface part 480*b* includes a part 480*c* positioned below the front surface 473*a*. For example, the front surface 473*a* of the nozzle 473 is positioned between the light emitter 710 and at least a part of the part 480*c*. In other words, the sterilizing light that is irradiated from the light emitter 710 is not irradiated directly on at least a part of the part 480*c*.

Figure 19B:
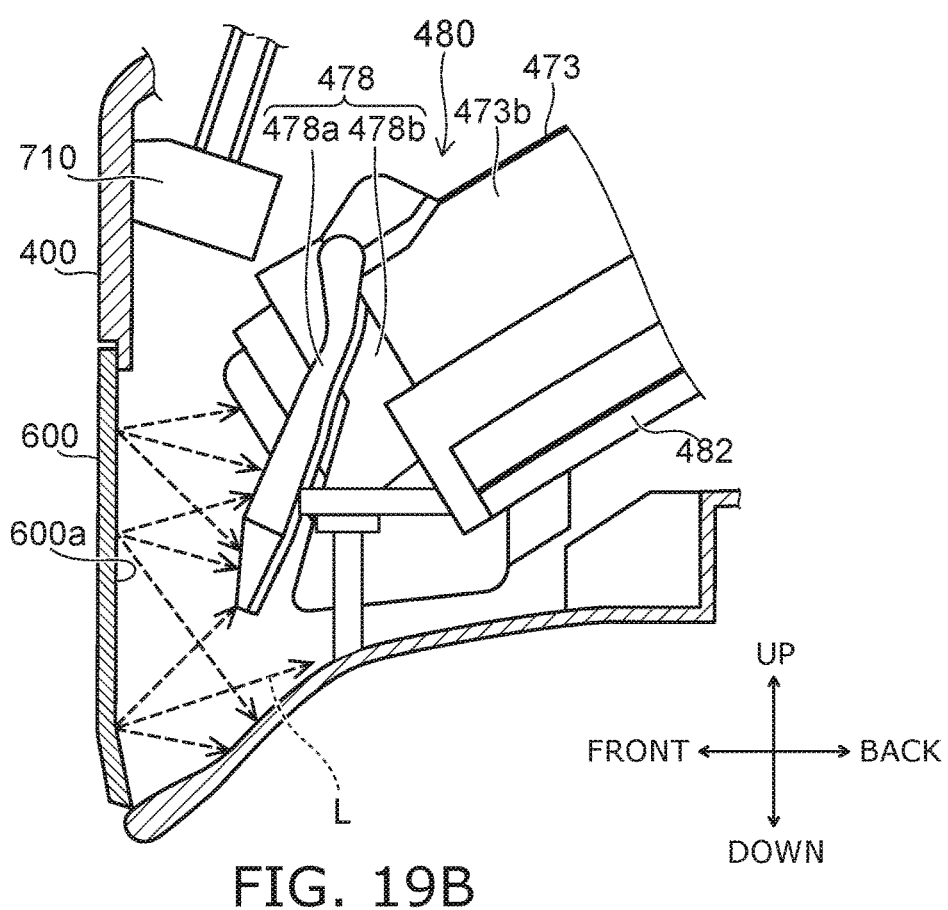

FIG. 19B illustrates the sterilizing light L irradiated from the light emitter 710 and reflected by the back surface 600*a*. When the sterilizing light L is irradiated on the back surface 600*a*, a part of the sterilizing light L is reflected as illustrated in FIG. 19B. For example, the sterilizing light L that is reflected by the back surface 600*a* is irradiated on at least the front surface 473*a* of the nozzle 473 and the part of the nozzle container 480 positioned frontward of the front surface 473*a*. Specifically, the part of the nozzle container 480 positioned frontward of the front surface 473*a* includes the bottom surface part 480*b* and a part of the nozzle washer 478.

By irradiating the sterilizing light L on the front surface 473*a* and the part 480*c*, the adhesion of dirt in the visible region which is the region of the nozzle 473 and the nozzle container 480 visible to the user can be suppressed. Thereby, the user can be caused to perceive that the nozzle 473 is clean and the nozzle container 480 where the nozzle 473 is stored is clean. Therefore, even a highly cleanliness-conscious user can use the private part wash nozzle with peace of mind.

The nozzle 473 has an outer perimeter surface 473*b* extending along the advance/retreat direction of the nozzle 473. For example, the nozzle 473 has a circular columnar configuration extending along the advance/retreat direction; and the outer perimeter surface 473*b* is curved. It is desirable for the illuminator 700 to be configured to cause the average illuminance of the sterilizing light L on the front surface 473*a* and the part of the nozzle container 480 positioned frontward of the front surface 473*a* to be larger than the average illuminance of the sterilizing light L on the outer perimeter surface 473b. Or, it is desirable for the illuminator 700 to be configured to cause the irradiation area of the sterilizing light L on the front surface 473a and the part of the nozzle container 480 positioned frontward of the front surface 473a to be wider than the irradiation area of the sterilizing light L on the outer perimeter surface 473b.

Thereby, the sterilizing light L is irradiated with particular emphasis on the visible region of the nozzle 473 and the nozzle container 480. Therefore, dirt adheres less easily in the visible region where high cleanliness is necessary. In recent years, it has become desirable to downsize the sanitary washing device 100 to improve the designability. According to the relationship of the average illuminance or the irradiation area described above, the unnecessary irradiation of the sterilizing light L can be suppressed; and the electrical power that is applied to the illuminator 700 can be small. The heat generation of the illuminator 700 decreases as the electrical power decreases. Thereby, the heat sink that dissipates the heat of the illuminator 700, etc., can be small; and the illuminator 700 can be downsized. As a result, the sanitary washing device 100 can be downsized. Dirt does not adhere easily to the outer perimeter surface 473b of the nozzle 473 due to the sterilizing water and/or the water discharged from the nozzle washer 478. Therefore, the adhesion of dirt to the outer perimeter surface 473b can be suppressed even without particular emphasis on irradiating the sterilizing light L.

It is desirable for at least a part of the back surface 600a to be formed of a reflective material to increase the irradiation intensity of the sterilizing light L or widen the irradiation area on the front surface 473a, etc. More desirably, the entire back surface 600a is formed of the reflective material. For example, the reflectance of the back surface 600a is larger than the reflectance of the bottom surface part 480b or the reflectance of the casing 400 inner surface adjacent to the back surface 600a. Similarly to the material of the reflector 740 described above, a metal material, a resin material having a high reflectance, or the like is used as the reflective material. For example, it is desirable to perform mirror finishing of the back surface 600a.

The adhesion of dirt to the back surface 600a can be suppressed by directly irradiating the sterilizing light L on the back surface 600a. The back surface 600a faces a wide area of the visible region such as the front surface 473a of the nozzle 473, the nozzle washer 478, the bottom surface part 480b, etc. By forming the back surface 600a of the reflective material, the sterilizing light L that is reflected by the back surface 600a is irradiated in a wide area of the visible region. Thereby, the sterilizing light L can be irradiated in a wide area of the visible region even when the illuminator 700 (the light emitter 710) is downsized.

In addition to the back surface 600a, the bottom surface part 480b and the inner surface of the casing 400 adjacent to the back surface 600a also may be configured to reflect the sterilizing light L. According to this configuration, the sterilizing light L can be irradiated in a wider area of the visible region.

It is desirable for the illuminator 700 to be configured to cause the irradiation area of the sterilizing light L directly irradiated on the back surface 600a to be wider than the irradiation area of the sterilizing light L directly irradiated on the part of the interior of the casing 400 other than the back surface 600a. By increasing the irradiation area of the sterilizing light L directly irradiated on the back surface 600a, the sterilizing light L that is reflected by the back surface 600a can be irradiated in a wider area of the visible region.

Reflected light and direct light are included in the sterilizing light L irradiated on the components inside the casing 400. The reflected light is the sterilizing light L reflected by the back surface 600a after being irradiated from the light emitter 710. The direct light is the sterilizing light L that is irradiated from the light emitter 710 and is directly irradiated without being reflected by the back surface 600a and/or the other members. It is desirable for the illuminator 700 to be disposed at a position such that the direct light is irradiated on a front end part 480d of the bottom surface part 480b. The front end part 480d includes, for example, the range within 10 mm toward the back from the front end of the bottom surface part 480b.

As a result of investigations, the inventors discovered that the water remaining inside the nozzle container 480 occurs easily at the front end part 480d of the bottom surface part 480b. The inventors discovered that the front end part 480d is dirtied most easily. The occurrence of bacteria and mold on the front end part 480d can be suppressed by irradiating direct light that has a strong sterilizing power on the front end part 480d which is the visible region where dirt occurs most easily. The front end part 480d can be kept clean thereby.

It is more desirable for the illuminator 700 to be disposed so that the direct light and the reflected light are irradiated on the front end part 480d. According to this configuration, both the direct light and the reflected light are irradiated on the front end part 480d where the dirt occurs most easily. Therefore, the occurrence of bacteria and mold at the front end part 480d which is the visible region where the remaining water occurs easily can be suppressed further.

Figure 20:
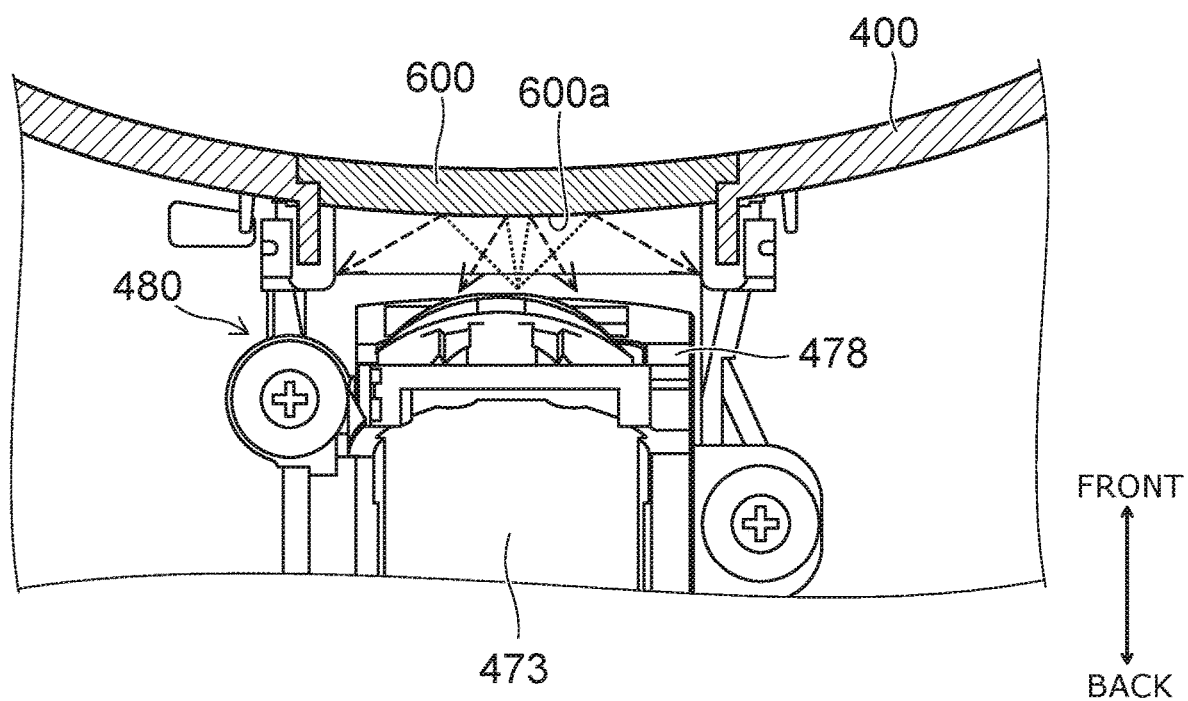
FIG. 20 is a plan view illustrating the private part wash nozzle periphery of the sanitary washing device according to another embodiment.

FIG. 20 is a plan view illustrating the private part wash nozzle periphery of the sanitary washing device according to another embodiment.

Figure 21:
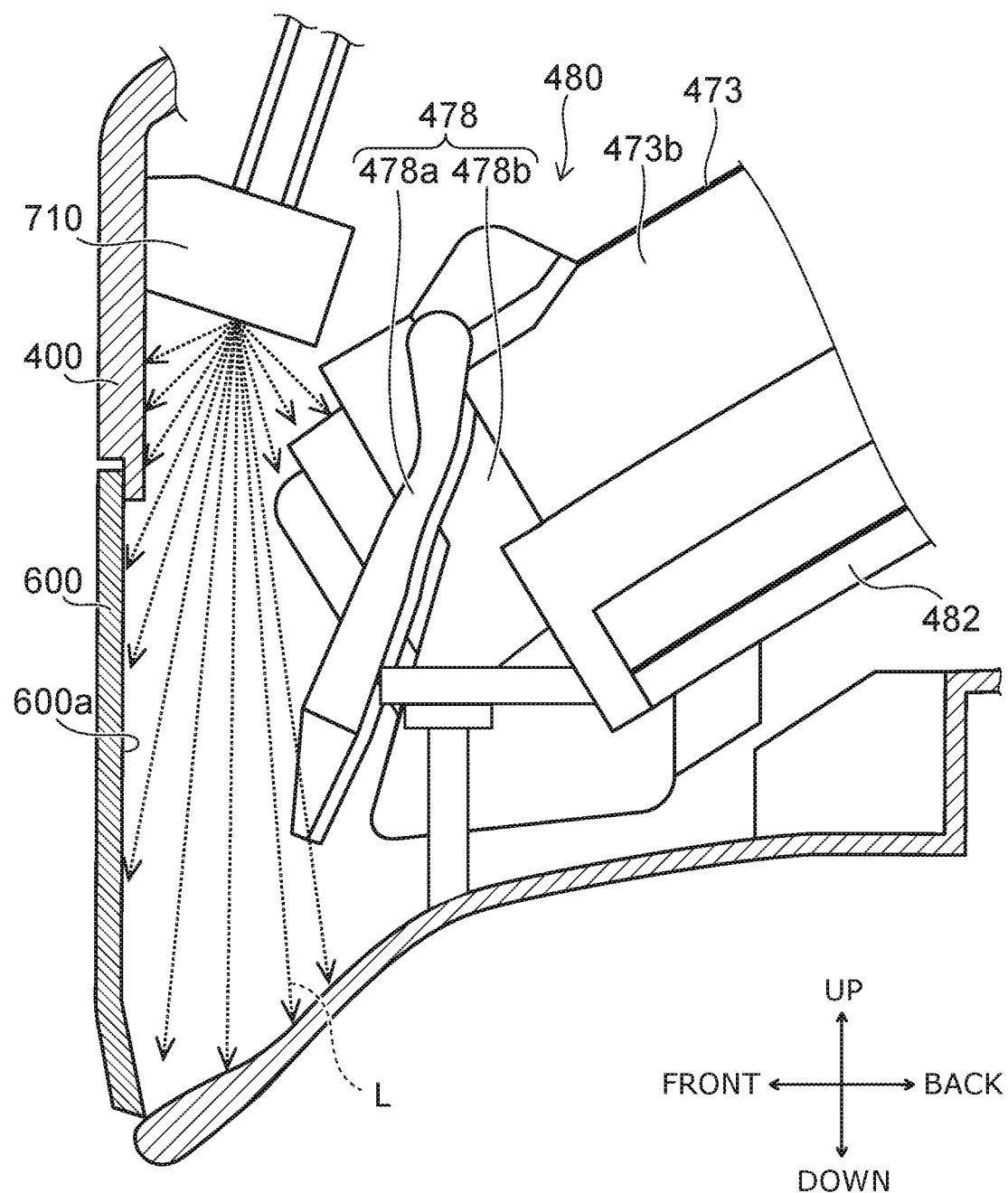
FIG. 21 and FIGS. 22A and 22B are cross-sectional views illustrating the private part wash nozzle periphery of the sanitary washing device according to the other embodiment.
Figure 22A:
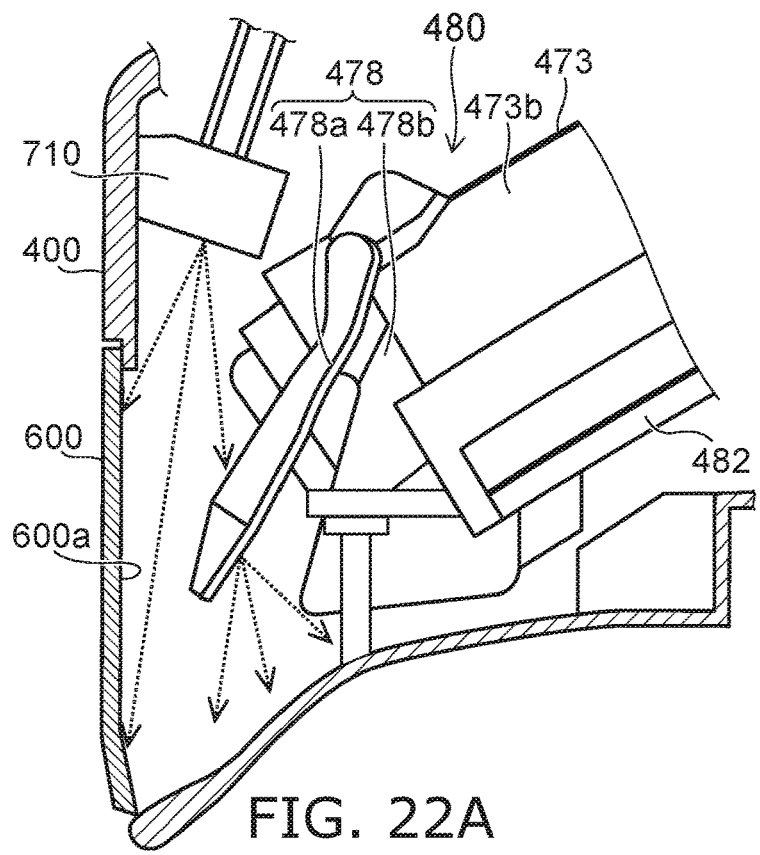
Figure 22B:
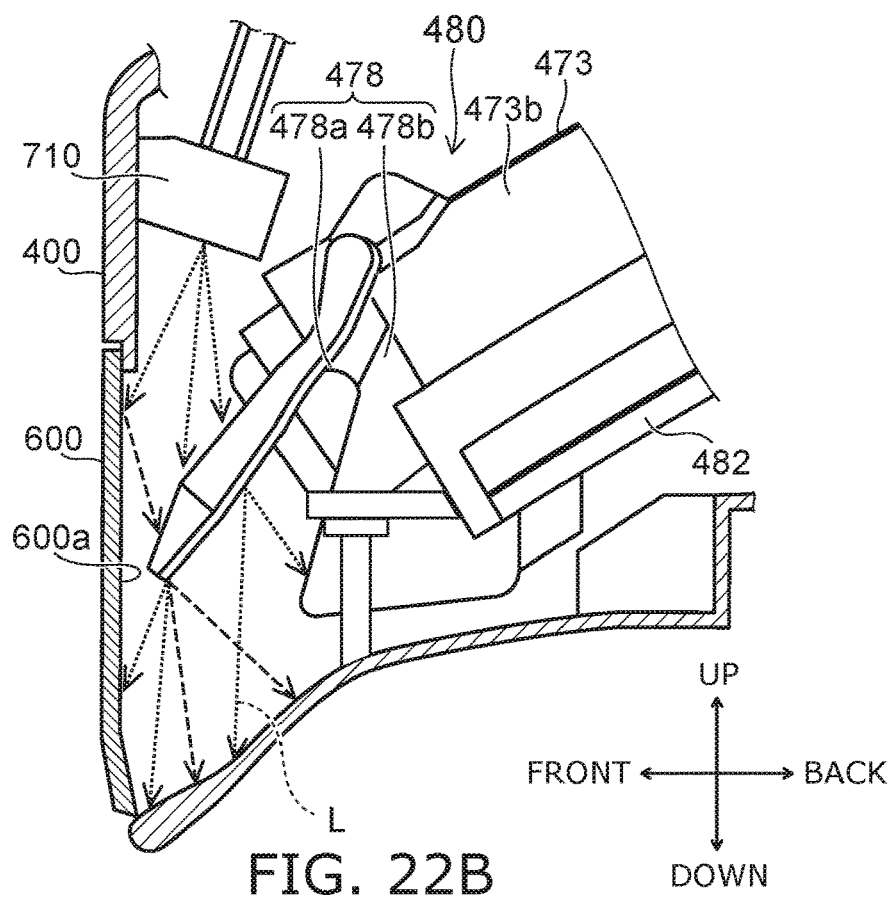

FIG. 21 and FIGS. 22A and 22B are cross-sectional views illustrating the private part wash nozzle periphery of the sanitary washing device according to the other embodiment.

As illustrated in FIG. 20, it is desirable for the back surface 600a of the nozzle lid 600 to be formed in a curved configuration to diffuse the reflected light. The sterilizing light L can be diffused more when reflected by the back surface 600a according to this configuration than by a planar back surface 600a. Thereby, the sterilizing light L can be irradiated in a wider area of the visible region.

It is desirable for the nozzle washer 478 to be formed of a transmissive material. In other words, as illustrated in FIG. 21, it is desirable for the sterilizing light L to pass through the nozzle washer 478. The nozzle washer 478 is provided at the front end part of the nozzle 473. Therefore, the sterilizing light L that passes through the nozzle washer 478 is irradiated in the visible region positioned in the shadow of the light emitter 710 and in the gap between the nozzle 473 and the nozzle washer 478. Thereby, the sterilizing light can be irradiated on a wider area of the visible region. For example, it is desirable for the transmittance of the nozzle washer 478 to be 5% or more.

More desirably, the nozzle washer 478 is configured so that the sterilizing light L is diffused when being transmitted. For example, the nozzle washer 478 is formed of a resin to which a scattering agent is added. At least a part of the nozzle washer 478 is positioned frontward of the front surface 473a in the state in which the entire nozzle 473 is stored inside the nozzle container 480. Therefore, when the sterilizing light L is diffused by the nozzle washer 478, the sterilizing light L can be irradiated in a wider area of the visible region. For example, the illuminance of the sterilizing light L in the visible region positioned in the shadow of the illuminator 700 can be large.

The nozzle washer 478 may be moved in the state in which the sterilizing light L is irradiated by operating the illuminator 700. When the nozzle washer 478 is moved when operating the illuminator 700, the irradiation area of the sterilizing light L changes as illustrated in FIG. 22A and FIG. 22B. Thereby, the sterilizing light L can be irradiated in a wider area of the visible region. For example, the nozzle washer 478 is moved by sliding the nozzle 473. A driver that drives the nozzle washer 478 may be provided. The nozzle washer 478 is moved by operating the driver.

More desirably, the nozzle washer 478 is moved without opening the nozzle lid 600 when operating the illuminator 700. Thereby, the leaking of the sterilizing light L outside the casing 400 can be suppressed; and the sterilizing light can be irradiated on a wider area of the visible region while increasing the safety of the user.

Herein, an example is described in which the sanitary washing device 100a includes the nozzle lid 600. The sanitary washing device 100a may not include the nozzle lid 600. In such a case, the visible region is a region visible to the user through the opening where the private part wash nozzle advances or retracts. When the sanitary washing device 100 or 100a includes the nozzle lid 600, the visible region is a region visible to the user when the nozzle lid 600 is fully open. If the nozzle lid 600 is not provided, for example, the illuminator 700 is provided so that the sterilizing light L is irradiated directly on the front surface 473a of the nozzle 473 and/or the part 480c of the bottom surface part 480b positioned below the front surface 473a.

Hereinabove, embodiments of the invention are described. However, the invention is not limited to these descriptions. Appropriate design modifications made by one skilled in the art for the embodiments described above also are within the scope of the invention to the extent that the features of the invention are included. For example, the configurations, the dimensions, the materials, the arrangements, the mounting methods, etc., of the components included in the sanitary washing device 10, etc., are not limited to those illustrated and can be modified appropriately.

Also, the components included in the embodiments described above can be combined within the limits of technical feasibility; and such combinations are within the scope of the invention to the extent that the features of the invention are included.

What is claimed is:

1. A sanitary washing device, comprising:
a private part wash nozzle tilted downward toward a front side, the private part wash nozzle having a water discharge hole discharging washing water toward a private part of a user;
a nozzle motor causing the private part wash nozzle to advance and retract;
a casing including a nozzle container configured to store an entirety of the private part wash nozzle in a state in which the private part wash nozzle is retracted; and
an illuminator irradiating sterilizing light, the sterilizing light being light having a sterilizing action,
the illuminator irradiating the sterilizing light on at least a front surface of the private part wash nozzle and a part of a bottom surface part of the nozzle container positioned below the front surface.

2. The device according to claim 1, wherein at least a part of the illuminator is provided frontward of the front surface of the private part wash nozzle to cause an average illuminance of the sterilizing light on the front surface and a part of the nozzle container positioned frontward of the front surface to be larger than an average illuminance of the sterilizing light on an outer perimeter surface of the private part wash nozzle.

3. The device according to claim 1, wherein at least a part of the illuminator is provided frontward of the front surface of the private part wash nozzle to cause an irradiation area of the sterilizing light on the front surface and a part of the nozzle container positioned frontward of the front surface to be wider than an irradiation area of the sterilizing light on an outer perimeter surface of the private part wash nozzle.

4. The device according to claim 1, further comprising a nozzle lid provided to be openable and closable with respect to an opening provided at a front end of the nozzle container, the nozzle lid causing the nozzle container to be open in a state in which the private part wash nozzle is advanced and causing the nozzle container to be closed in a state in which the entirety of the private part wash nozzle is stored inside the nozzle container,
the nozzle lid having a back surface positioned on the nozzle container side,
at least a part of the back surface being formed of a reflective material,
the illuminator directly irradiating at least a part of the sterilizing light on the back surface of the nozzle lid in a state in which the nozzle lid is closed.

5. The device according to claim 4, wherein the illuminator is provided in a vicinity of the back surface of the nozzle lid to cause an irradiation area of the sterilizing light directly irradiated on the back surface of the nozzle lid to be wider than an irradiation area of the sterilizing light directly irradiated on a part of the nozzle lid other than the back surface.

6. The device according to claim 4, wherein
the sterilizing light includes reflected light reflected by the nozzle lid, and direct light not reflected by the nozzle lid, and
the illuminator is disposed at a position to cause the direct light to be irradiated on a front end part of the bottom surface part of the nozzle container.

7. The device according to claim 6, wherein the illuminator is disposed to cause the direct light and the reflected light to be irradiated on the front end part of the bottom surface part.

8. The device according to claim 4, wherein the back surface of the nozzle lid is formed in a curved configuration to cause reflected light to diffuse.

9. The device according to claim 4, wherein
a nozzle washer is provided at a front end part vicinity of the private part wash nozzle,
the nozzle washer has a nozzle wash hole discharging washing water onto an outer surface of the private part wash nozzle, and
the nozzle washer is formed of a transmissive material transmitting the sterilizing light.

10. The device according to claim 9, wherein
the nozzle washer includes a scattering agent to cause the sterilizing light to diffuse when being transmitted, and
at least a part of the nozzle washer is disposed frontward of the front surface of the private part wash nozzle in a state in which the entirety of the private part wash nozzle is stored inside the nozzle container.

11. The device according to claim 10, wherein the nozzle washer is moved in a state in which the illuminator is operated.

12. The device according to claim 11, wherein the nozzle washer is moved without opening the nozzle lid in the state in which the illuminator is operated.

\* \* \* \* \*